US007220269B1

(12) United States Patent
Ansel et al.

(10) Patent No.: US 7,220,269 B1
(45) Date of Patent: May 22, 2007

(54) THROMBECTOMY CATHETER SYSTEM WITH OCCLUDER AND METHOD OF USING SAME

(75) Inventors: Gary M. Ansel, Columbus, OH (US); Michael J. Bonnette, Minneapolis, MN (US); Dan T. Janse, Lino Lakes, MN (US); Hieu V. Le, Minneapolis, MN (US)

(73) Assignee: Possis Medical, Inc., Minneapolis, MN (US)

( * ) Notice: Subject to any disclaimer, the term of this patent is extended or adjusted under 35 U.S.C. 154(b) by 99 days.

(21) Appl. No.: 10/702,815

(22) Filed: Nov. 6, 2003

(51) Int. Cl.
*A61B 17/3203* (2006.01)
*A61B 17/3207* (2006.01)
*A61M 25/14* (2006.01)

(52) U.S. Cl. .................... 606/159; 604/22; 604/35; 604/43; 604/500

(58) Field of Classification Search ............. 606/200, 606/159, 114, 127, 128, 168; 604/101.04, 604/35, 22, 43
See application file for complete search history.

(56) References Cited

U.S. PATENT DOCUMENTS

| 4,690,672 | A | * | 9/1987 | Veltrup | 604/43 |
|---|---|---|---|---|---|
| 5,370,609 | A | * | 12/1994 | Drasler et al. | 604/22 |
| 5,785,675 | A | * | 7/1998 | Drasler et al. | 604/22 |
| 5,941,871 | A | * | 8/1999 | Adams et al. | 604/523 |
| 5,971,938 | A | * | 10/1999 | Hart et al. | 600/562 |
| 5,989,271 | A | * | 11/1999 | Bonnette et al. | 606/159 |
| 6,080,170 | A | * | 6/2000 | Nash et al. | 606/159 |
| 6,096,001 | A | * | 8/2000 | Drasler et al. | 604/22 |
| 6,135,977 | A | * | 10/2000 | Drasler et al. | 604/22 |
| 6,176,844 | B1 | * | 1/2001 | Lee | 604/101.04 |
| 6,206,868 | B1 | * | 3/2001 | Parodi | 604/500 |
| 6,258,061 | B1 | * | 7/2001 | Drasler et al. | 604/131 |
| 6,485,500 | B1 | * | 11/2002 | Kokish et al. | 606/194 |
| 6,485,502 | B2 | * | 11/2002 | Don Michael et al. | 606/200 |
| 6,491,660 | B2 | * | 12/2002 | Guo et al. | 604/35 |
| 6,524,323 | B1 | * | 2/2003 | Nash et al. | 606/159 |
| 6,544,209 | B1 | * | 4/2003 | Drasler et al. | 604/22 |
| 6,805,684 | B2 | * | 10/2004 | Bonnette et al. | 604/22 |

* cited by examiner

*Primary Examiner*—Anhtuan T. Nguyen
*Assistant Examiner*—Elizabeth Houston
(74) *Attorney, Agent, or Firm*—Hugh D. Jaeger, Esq.

(57) ABSTRACT

A thrombectomy catheter system with occluder and method of using same for removal of tissue, such as thrombus and the like, from a vessel in the body. Multiple catheters and an occluder-bearing guidewire tube at a thrombus site provide for expandable deployment of a compliant occluder against the vasculature walls distal to the thrombus. The expanded occluder is maneuvered proximally to urge thrombus into close proximity with a retractable capture cone located distally on a capture catheter where the thrombus is dislodged, entrained, and broken into pieces by the action of a fluid jet emanator and then evacuated through the capture catheter.

24 Claims, 27 Drawing Sheets

THROMBECTOMY CATHETER SYSTEM WITH OCCLUDER AND METHOD OF USING SAME

CROSS REFERENCES TO RELATED APPLICATIONS

None.

BACKGROUND OF THE INVENTION

1. Field of the Invention

The present invention is for a thrombectomy catheter system with occluder and method of using same.

2. Description of the Prior Art

Prior art devices for addressing and influencing thrombotic deposits often included angioplasty devices where thrombotic deposits were merely reshaped outwardly and the vessel surrounding the thrombotic material was correspondingly urged to expand to allow greater blood throughflow. Such devices were often equipped with a filter or a balloon-style occluder distal to the thrombotic occlusion to filter out or constrain any thrombotic material which may be dislodged during such reshaping angioplasty processes to prevent recirculation of such thrombotic material in the vasculature. Often an occluder-like balloon would be utilized distal to the thrombotic deposit from which a cleansing fluid would be discharged in a less than aggressive fashion in order to carry any dislodged thrombotic material proximally to a collection device. While performing angioplasty involving the reshaping of the thrombotic material, little was done to actively and aggressively cause thrombotic materials to be urged into maceration devices for breaking up and carrying away the thrombotic materials. Such a function is provided by the present invention.

SUMMARY OF THE INVENTION

The general purpose of the present invention is to provide a thrombectomy catheter system with occluder and method of using same.

According to the present invention, there is provided a thrombectomy catheter system with occluder and method of using same for removal of tissue, such as thrombus and the like, from a vein or other vessel in the body. Several structures are provided for placement in a vein, artery or other vessel of the body to provide for removal of thrombus or like material. One such structure is a guide catheter attached to a manifold where the guide catheter is advanced into the vasculature to position the distal end of the guide catheter just proximal of a thrombus site. Another structure is an occluder guidewire tube having a distally located inflatable, expandable or distendable compliant occluder, which can be a balloon occluder or a mesh occluder, and a guidewire coil which is advanced distally through and beyond the distal end of the guide catheter to and through the thrombus at the thrombus site to a location whereat the occluder can be inflated, expanded or distended. Another structure includes a capture catheter suitably attached to a manifold that includes or supports at least the following components: a retractable capture cone being part of the capture catheter structure and being distally located on the capture catheter, a high pressure or hypo tube having a distally located fluid jet emanator, and a hemostasis nut. The retractable capture cone and the fluid jet emanator fixedly co-locate distally at the distal end of the capture catheter. The distal end of the capture catheter with the co-located retractable capture cone and fluid jet emanator are advanced distally over and about the occluder guidewire tube and within the guide catheter to be positioned distally just beyond the distal end of the guide catheter and just proximal to the thrombus site where the retractable capture catheter cone is expandingly deployed in a cone shape against the artery, vein or other vessel wall. Expanded deployment of the retractable capture cone provides a structure to receive displaced thrombus for breakup and maceration by the fluid jet emanator, which provides proximally directed fluid jet streams. The occluder, which could distend, expand or inflate, compliantly conforms to the shape of the vein wall or other vessel wall and is maneuvered proximally by maneuvering the occluder guidewire tube proximally, thereby urging and displacing the thrombus proximally into or near the deployed retractable capture cone where the thrombus comes into contact with and is impinged by the proximally directed fluid jet streams of the fluid jet emanator for breakup and maceration and subsequent evacuation through the capture catheter.

The method of use of the present invention incorporates the following steps:

1. Advancing the distal end of the guide catheter into a blood vessel or other vessel to a position just proximal of a thrombus buildup.

2. Loading and advancing the distal end of the occluder guidewire tube through the hemostasis nut and into and through a manifold and thence through a lumen of the guide catheter.

3. Advancing the distal end of the occluder guidewire tube including the guidewire coil and the occluder beyond the distal end of the guide catheter and through and beyond the thrombus.

4. Loading the distal end of the capture catheter, including the retractable capture cone and the fluid jet emanator, over the proximal end of the occluder guidewire tube.

5. Inflating, expanding or distending the occluder to occlude the blood vessel or other vessel.

6. Positioning the capture catheter to a position to expandingly deploy the retractable capture cone just beyond the distal end of the guide catheter.

7. Providing and activating high pressure medium to the fluid jet emanator to form rearwardly directed fluid jets.

8. Positioning the expanded, inflated or distended occluder proximally to impinge, impact, dislodge, reshape and redistribute thrombus and to urge and deliver such thrombus into the retractable capture cone.

9. Macerating, dislodging, reducing and breaking up repositioned thrombus delivered to the retractable capture cone by interaction of the rearwardly directed fluid jets with the thrombus.

10. Evacuating the macerated, dislodged, reduced and broken-up thrombus.

Discussion of the above steps is provided with reference to FIGS. 1 and 13–17.

According to embodiments of the present invention, there are provided thrombectomy catheter systems with occluders.

One significant aspect and feature of the present invention is a thrombectomy catheter system with occluder incorporating a guide catheter.

Another significant aspect and feature of the present invention is a thrombectomy catheter system with occluder incorporating a capture catheter having a retractable capture cone.

Still another significant aspect and feature of the present invention is a thrombectomy catheter system with occluder incorporating expansion struts to expand a retractable capture cone.

Another significant aspect and feature of the present invention is a thrombectomy catheter system with occluder having a retractable capture cone of expandable mesh.

Yet another significant aspect and feature of the present invention is a thrombectomy catheter system with occluder having a retractable capture cone which is deployable and which is retractable.

A further significant aspect and feature of the present invention is a thrombectomy catheter system with occluder having a retractable capture cone which receives and collects thrombus for breakup and maceration.

A further significant aspect and feature of the present invention is a thrombectomy catheter system with occluder having a fluid jet emanator co-located with a retractable capture cone which receives thrombus for breakup and maceration.

A still further significant aspect and feature of the present invention is a thrombectomy catheter system with occluder having an occluder guidewire tube having a distally located occluder which can be inflatable, deflatable, expandable, distendable, and compliant.

A still further significant aspect and feature of the present invention is a thrombectomy catheter system with occluder having a distally located occluder which can be inflated, expanded or distended, and which can be positioned by proximal movement of the occluder guidewire tube to urge thrombus into the retractable capture cone to come under the influence of a fluid jet emanator.

In alternative embodiments, another significant aspect and feature of the present invention is a controllable-shape mesh occluder for use with the thrombectomy catheter system with occluder.

In alternative embodiments, another significant aspect and feature of the present invention is a flexible shaped mesh occluder for use with the thrombectomy catheter system with occluder.

Having thus enumerated certain significant aspects and features of the present invention, it is the principal object of the present invention to provide a thrombectomy catheter system with occluder and method of using same.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
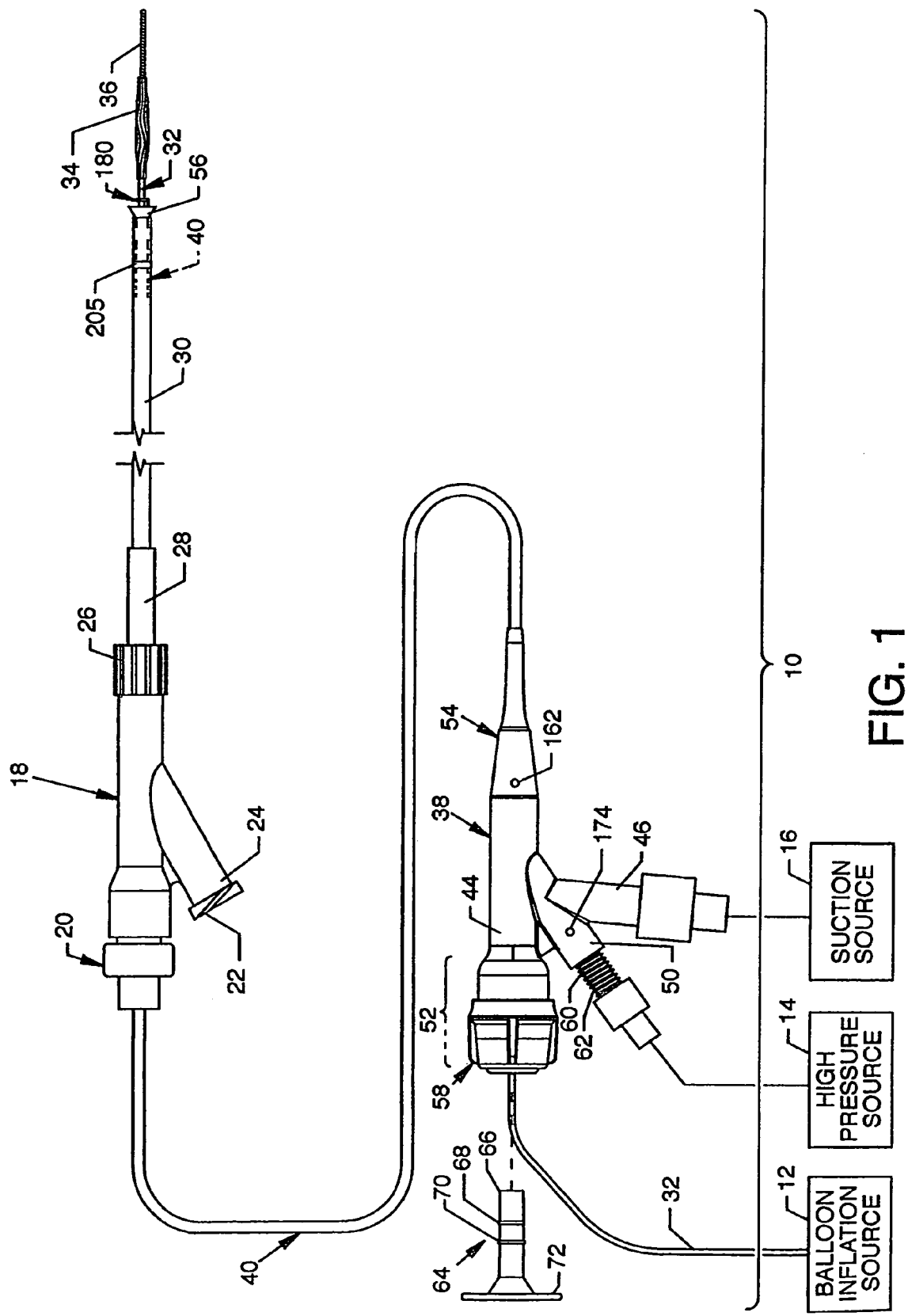
FIG. 1 is a plan view of the thrombectomy catheter system with occluder, the present invention, shown in use with supporting operational sources.
Figure 2:
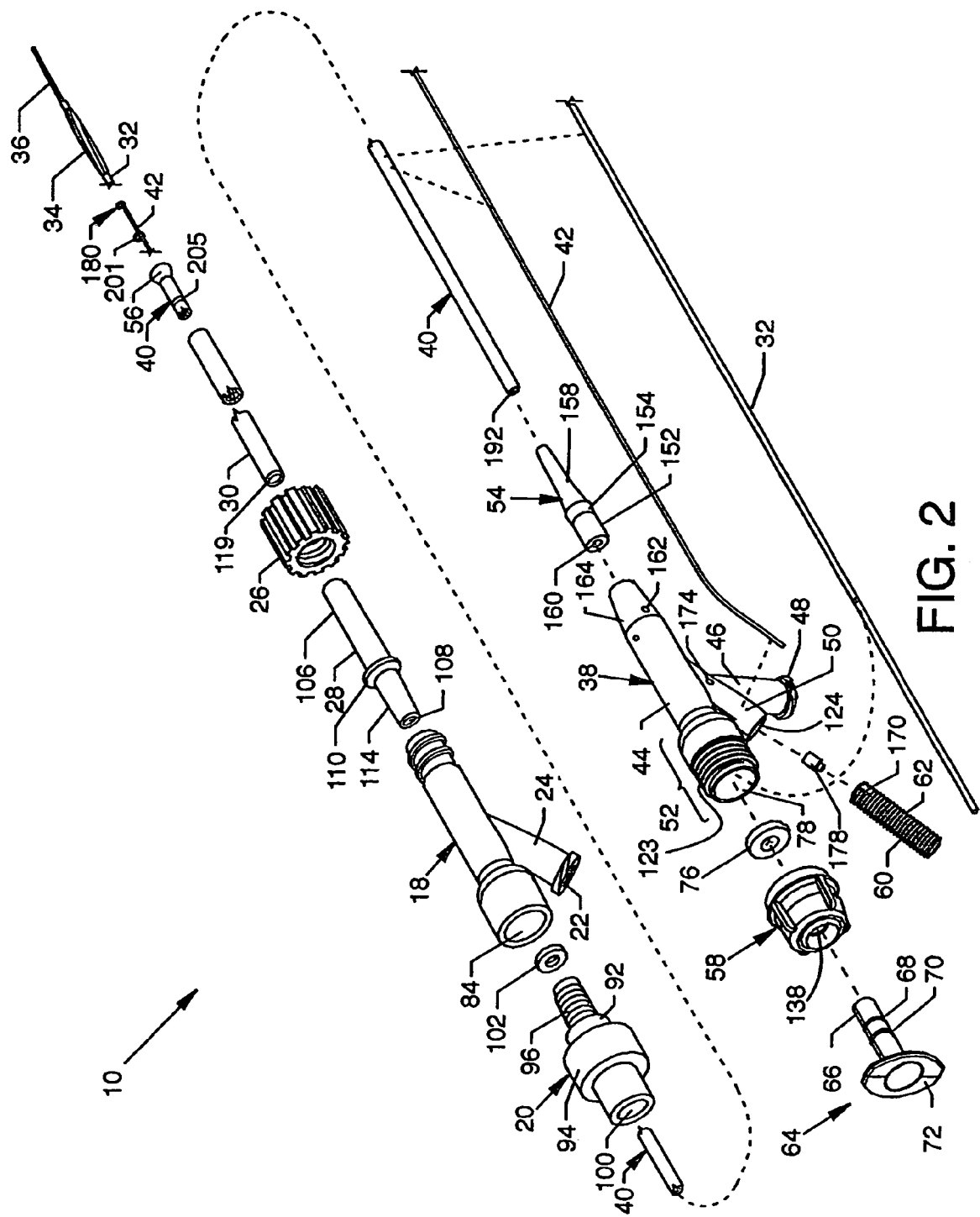
FIG. 2 is an exploded isometric view of the thrombectomy catheter system with occluder.

FIG. 1 is a plan view of the thrombectomy catheter system with occluder 10, the present invention, shown in use with supporting operational sources including, but not limited to, a balloon inflation source 12, a high pressure source 14, and a suction source 16. FIG. 2 is an exploded isometric view of the thrombectomy catheter system with occluder 10. With reference to FIGS. 1 and 2, structure of the present invention is now described. Externally visible components, or portions of components, of the thrombectomy catheter system with occluder 10, as illustrated in FIGS. 1 and 2, include a first structure including a manifold 18, also known as a Y-adapter, a hemostasis nut 20 which secures in the proximal end of the manifold 18, a Luer connection 22 located at the proximal end of an angled manifold branch 24 extending from the manifold 18, a Luer fitting 26 secured to the distal end of the manifold 18, a strain relief 28, which can be flexible, secured to the distal end of the manifold 18 by the Luer fitting 26, and a guide catheter 30 suitably attached to the distal end of the manifold 18 via the strain relief 28. Another structure is an occluder guidewire tube 32 having an occluder, in this embodiment in the form of a balloon occluder 34, which can be an elastomer similar to polyurethane, silicone, latex or the like, which is inflatable and deflatable and which is compliant. Alternatively, balloon occluder 34 can be an inflatable and deflatable balloon of stiffer polymeric materials such as polyester or PET or composite material, and which may unfold as it is inflated; for example, balloon occluder 34 can also function like an angioplasty balloon. Other embodiments show occluders which are non-inflatable, yet compliant. The balloon occluder 34 is located at the distal portion of the occluder guidewire tube 32. A guidewire coil 36, which is flexible, is located distal to the balloon occluder 34 and distal to the occluder guidewire tube 32. Another structure includes a one-piece manifold 38 having multiple components extending therefrom or attached thereto including a capture catheter 40, a high pressure tube 42, and other components as described herein. The visible portion of the one-piece manifold 38 includes a central tubular body 44, an exhaust branch 46 having branch passage 47 (FIG. 5) and a Luer connection 48 and a flangeless high pressure connection branch 50 extending angularly from the central tubular body 44, and a cavity body 52 extending proximally from the central tubular body 44. The proximal end of the capture catheter 40 secures to the manifold 38 by an interceding streamlined flexible strain relief 54. The proximal end of the capture catheter 40 extends through the streamlined flexible strain relief 54 to communicate with the manifold 38. The capture catheter 40 extends distally to include a distally located retractable capture cone 56, the retractable capture cone 56 being shown in the deployed and expanded position. Also shown is a hemostasis nut 58 aligned to and snappingly engaged with the proximal region of the cavity body 52, and a high pressure connection port 60 having threads 62 which is secured such as by, but not limited to, adhesive, to the high pressure connection branch 50. Also provided is an introducer 64 having a hollow shaft 66, annular rings 68 and 70 about the hollow shaft 66, and an actuating handle 72. A self-sealing hemostasis valve 76 aligns in cavity 78 located proximally in the cavity body 52 to seal about the occluder guidewire tube 32.

As used herein, the term guide catheter referring to it m 30 can be a standard guide catheter as is known in percutaneous interventions, but the meaning is intended to be more general, and to include any generally tubular element through which capture catheter 40, or variations or alternative embodiments thereof, can pass and which restrains the retractable capture cone 56, or variations or alternative embodiments thereof, when the retractable capture cone 56 is retracted within the tubular element. Guide catheter 30 can have other characteristics typical of other tubular elements such as guiding catheters, introducer sheaths, guiding sheaths, angiographic catheters, infusion catheters, and so forth, but must additionally provide for passage of the capture catheter 40, or variations or alternative embodiments thereof, and provide for restraining the retractable capture cone 56, or variations or alternative embodiments thereof, in an unexpanded configuration when retractable capture cone 56 is retracted therein. Variations or alternative embodiments of capture catheters, retractable capture cones, fluid jet emanators, occluders in the form of balloon occluders or mesh occluders and the like, are described later in detail which can be operated in the structures of the invention to perform similar functions within the teachings of the invention.

Figure 3:
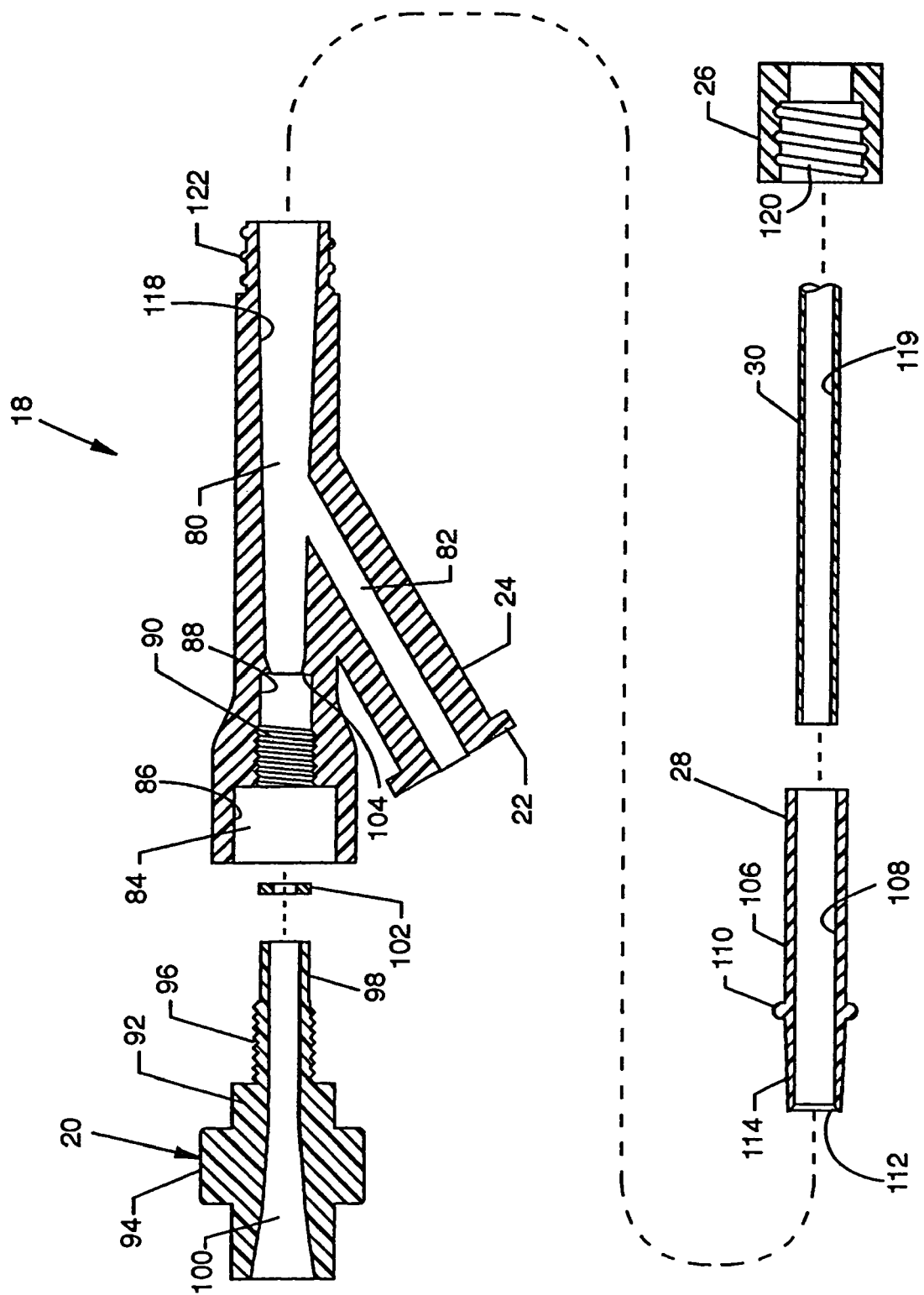
FIG. 3 is an exploded cross sectional side view of a manifold and associated components.

FIG. 3 is an exploded cross sectional side view of the manifold 18 and associated components. The manifold 18 includes a centrally located tapered passage 80 aligned along the longitudinal axis of the manifold 18 and a branch passage 82 which extends along the axis of the manifold branch 24 and which intersects with and is connected to the central tapered passage 80. The proximal end of the manifold 18 houses a multi-radius cavity 84 including a round outer cavity portion 86 and a connected round inner and smaller cavity portion 88 having a threaded surface 90 on the proximal portion thereof. The hemostasis nut 20 includes a body 92 having a grasping surface 94 extending thereabout, a threaded surface 96 extending from the body 92, an annular surface 98 at the end of the threaded surface 96, and a passageway 100 aligned centrally to the longitudinal axis of the hemostasis nut 20. The passageway 100 has a wide radius at the proximal end which decreases toward the distal end. The initial wide radius is helpful for insertion of the capture catheter 40, other guidewires, and the like. A seal 102 aligns to a distally located annular surface 104 of the round inner cavity portion 88 and bears around, about and against the annular surface 98 of the hemostasis nut 20 to seal the tapered passage 80 of the manifold 18 to the passageway 100 in the hemostasis nut 20, as required. The multi-radius cavity 84 and its internal geometry accommodate corresponding geometry of the hemostasis nut 20 and the seal 102.

Luer fitting 26 is utilized to secure the strain relief 28 and the guide catheter 30 to the distal end of the manifold 18. The strain relief 28 is comprised of a tube 106, a central bore 108 internal to the tube 106 which accommodates the guide catheter 30, an annular flange 110 about the tube 106, and a tapered proximal tube mouth end 112. It is to be noted that the outer diameter of the tube 106 is constant from the annular flange 110 to the distal end of the tube 106, and that the outer diameter steadily decreases from the annular flange 110 to the tapered proximal tube mouth end 112 to provide a tapered tube surface 114 which conforms, for purpose of a proper fit, to the taper of the tapered central passage surface 118 of the tapered passage 80. The tapered proximal tube mouth end 112 allows for easily accomplished alignment of the capture catheter 40, other guidewires or other assemblies within a lumen 119 located in the guide catheter 30. The Luer fitting 26 includes threads 120 which threadingly engage corresponding threads 122 at the distal end of the manifold 18. The Luer fitting 26 bears against the annular flange 110 of the strain relief 28 to force the tapered tube surface 114 of the strain relief 28 against the tapered central passage surface 118 of the tapered passage 80 to effect a suitable and stable seal.

Figure 4:
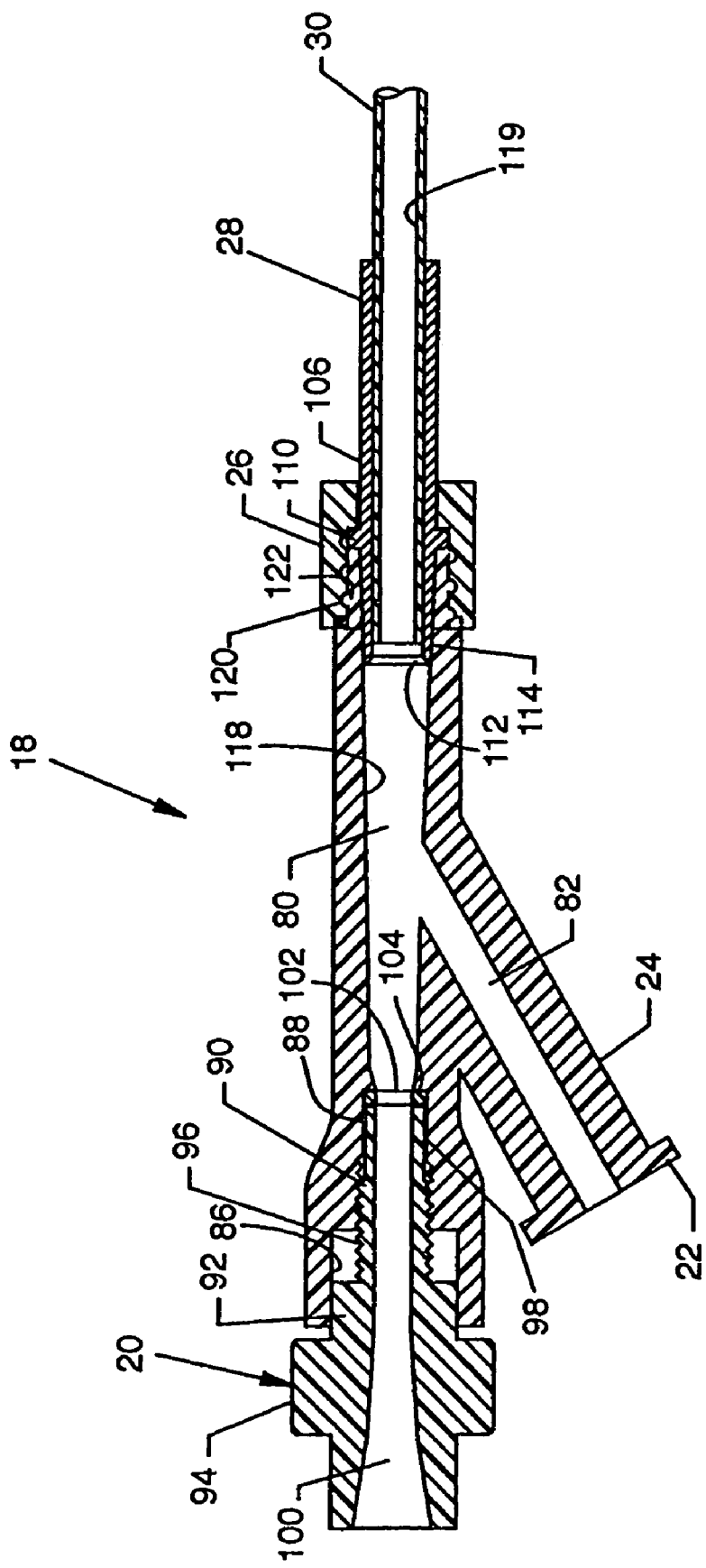
FIG. 4 is an assembled cross sectional side view of the manifold and associated components shown in FIG. 3.

FIG. 4 is an assembled cross sectional side view of the manifold 18 and associated components shown in FIG. 3.

Figure 5:
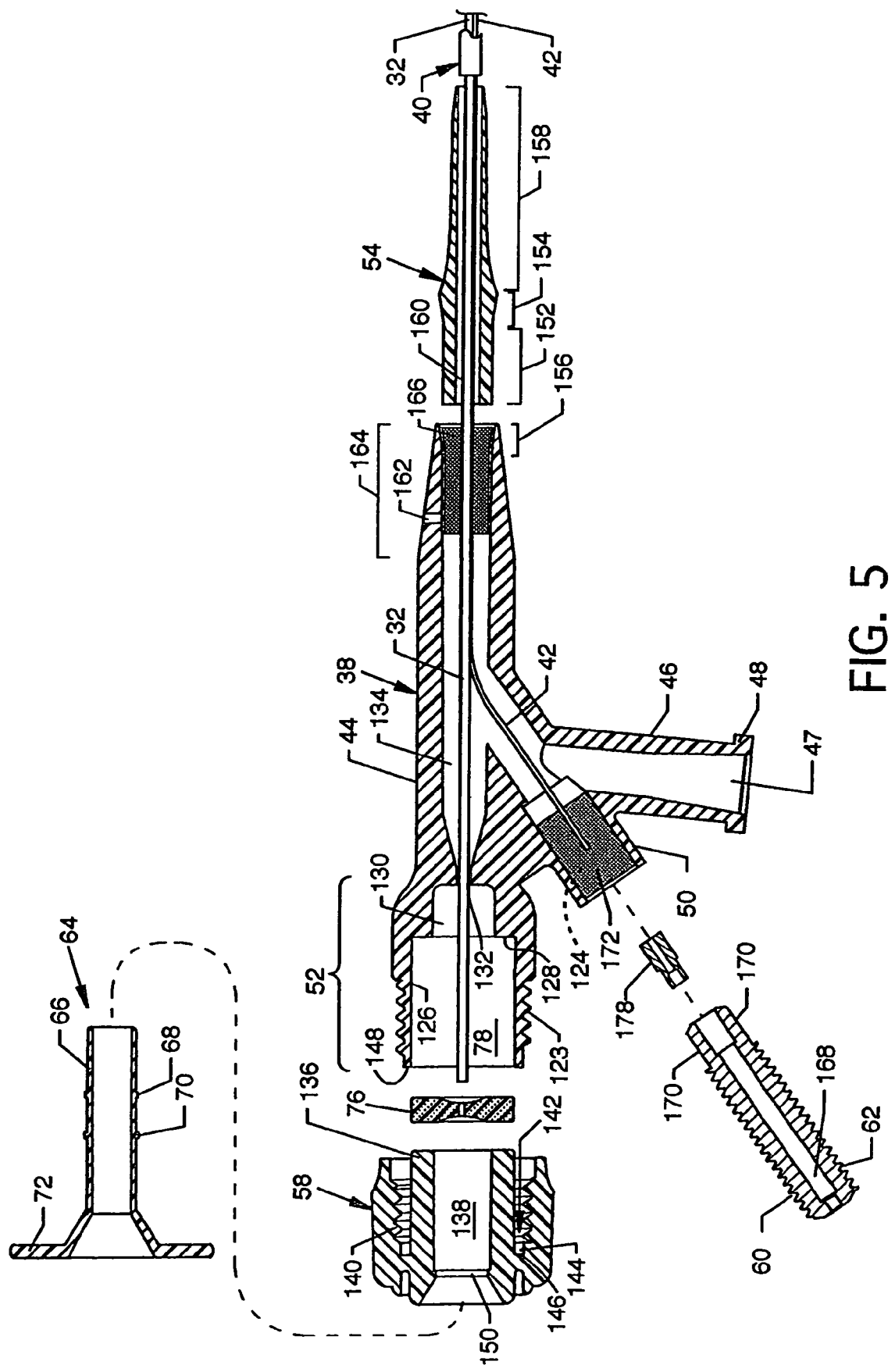
FIG. 5 is an exploded view in partial cross section of a manifold and associated components.
Figure 6:
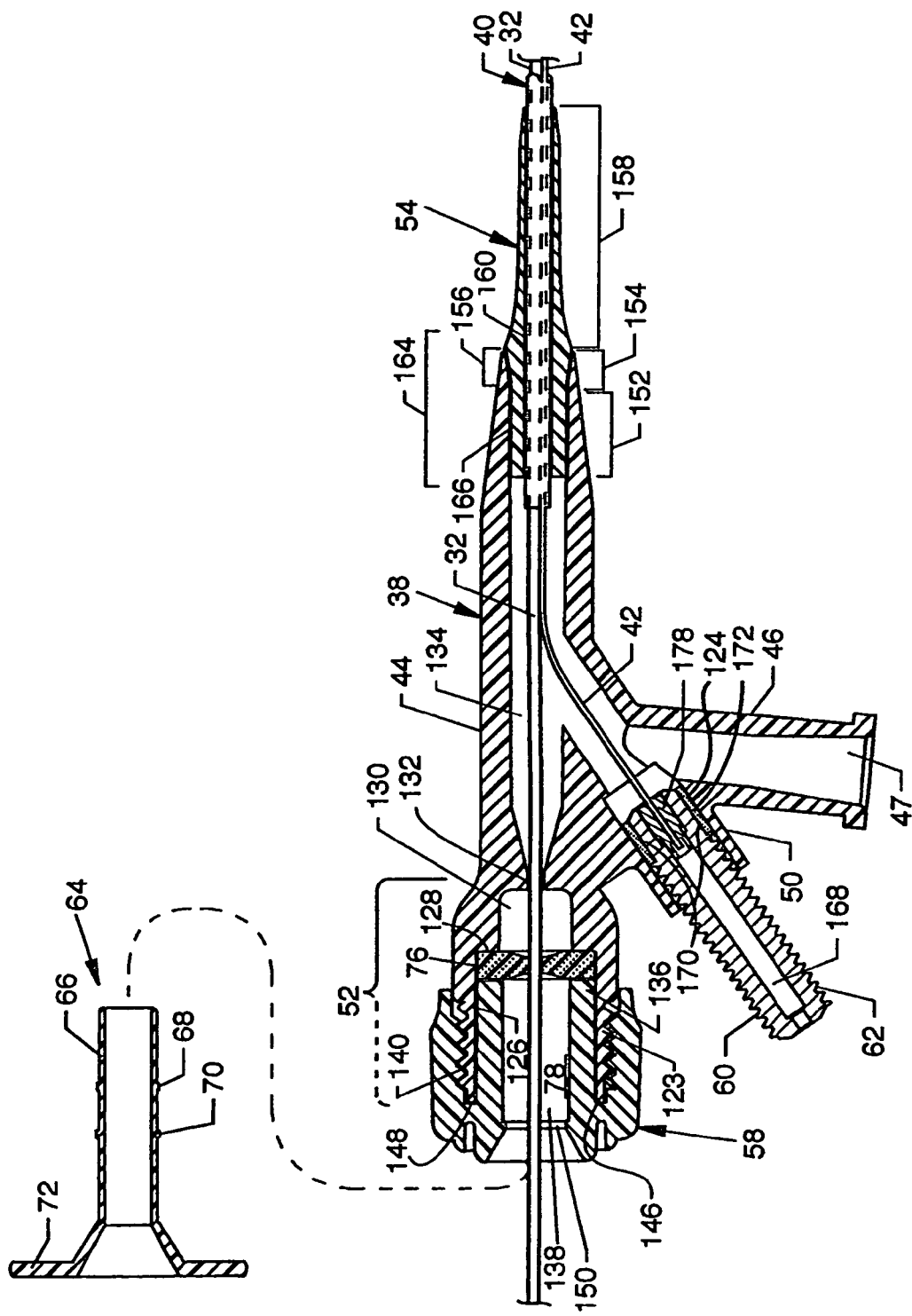
FIG. 6 is an assembled view in partial cross section of the components of the manifold and associated components shown in FIG. 5.

FIG. 5 is an exploded view in partial cross section of the manifold 38 and associated components, and FIG. 6 is an assembled view in partial cross section of the components of the manifold 38 and associated components shown in FIG. 5. A portion of the occluder guidewire tube 32 is also shown in engagement with the manifold 38 and other associated components.

The manifold 38 and associated components include a self-sealing hemostasis valve 76 and also a hemostasis nut 58 which aligns over and about threads 123 at the proximal region of the manifold 38. Portions of the hemostasis nut 58 and all of the self-sealing hemostasis valve 76 are accommodated internally by the cavity 78 located in the cavity body 52 of the manifold 38. The cavity 78 is for the most part tubular in shape including a tubular cavity wall 126 and a planar surface 128 which is annular and circular and which intersects the tubular cavity wall 126. A cavity extension 130, being for the most part tubular, extends distally from the cavity 78 beginning at the planar surface 128 to intersect and connect with an orifice 132. The orifice 132 is common to the cavity extension 130, the cavity 78, and a tapered central passageway 134 located central to the central tubular body 44. The cavity 78 accommodates the self-sealing hemostasis valve 76, which aligns to planar surface 128.

The hemostasis nut 58, which can provide a slidable seal about the occluder guidewire tube 32, includes a centrally located cylindrical boss 136, a beveled passageway 138 extending through and in part forming the cylindrical boss 136, and internal threads 140 distanced from the cylindrical boss 136 by a distally located space 142 extending along the internal threads 140 and along the distal portion of the cylindrical boss 136. A proximally located space 144 is located adjacent to the distally located space 142. An annular stop surface 146 is located at the proximal region of the proximally located space 144. The distally located space 142 accommodates the proximal end 148 of the manifold 38 including threads 123 located along and about the outer proximal portion of the cavity body 52 of the manifold 38. Also included in the hemostasis nut 58 is an annular lip 150 which can be utilized for snap engagement of the introducer 64 or other particular styles or types of introducers as required. The hemostasis nut 58 threadingly engages the manifold 38 where the internal threads 140 of the hemostasis nut 58 engage and are advanced along the threads 123 of the manifold 38 until advancement of the hemostasis nut 58 is predeterminately stopped by impingement of the annular stop surface 146 against the proximal end 148 of the manifold 38, whereby and whereupon the cylindrical boss 136 is brought to bear directly against the self-sealing hemostasis valve 76 resultingly bringing pressure to bear as required against the self-sealing hemostasis valve 76 to effect sealing with the cavity wall 126 of the cavity 78, to seal the self-sealing hemostasis valve 76 to the occluder guidewire tube 32 and to seal the self-sealing hemostasis valve 76 to the planar surface 128. In the alternative, a suitable adhesive can be applied to the internal threads 140 of the hemostasis nut 58 and/or to the threads 123 of the manifold 38 to ensure permanent fixation of the hemostasis nut 58 to the manifold 38. Such adhesive application ensures fixed and non-adjustable sealing of the self-sealing hemostasis valve 76 to the occluder guidewire tube 32. The self-sealing hemostasis valve 76 is captured in the cavity 78 by engagement of the hemostasis nut 58 to the cavity body 52 of the manifold 38, as shown in FIG. 6. Due to the similar geometrical configurations of the opposing faces and associated structure therebetween of the self-sealing hemostasis valve 76, the self-sealing hemostasis valve 76 can be inserted into the cavity 78 without regard to the orientation of the opposing sides.

The streamlined flexible strain relief 54 is fitted and adhesively or otherwise suitably affixed to the distal interior portion of the manifold 38. The streamlined flexible strain relief 54 can be fashioned of flexible plastic, rubber, or the like and includes a constant radius region 152 adjoined by a short tapered region 154, each region fitting to and being accommodated respectively by the distal portion of the tapered central passageway 134 and an included short tapered region 156 of the tapered central passageway 134 of the manifold 38, as shown in FIG. 6. Adjoining the short tapered region 154 of the streamlined flexible strain relief 54 is a tapered region 158 located distally thereto. A passageway 160 extends along the length of the streamlined flexible strain relief 54 for accommodation and passage of the occluder guidewire tube 32 and the high pressure tube 42. An adhesive injection port 162 (see also FIG. 1) can be located at a suitable location extending through an exterior tapered region 164 of the manifold 38, which is flangeless, to introduce adhesive 166 to the distal interior region of the manifold 38 including the distal end of the tapered central passageway 134 and the included short tapered region 156 of the tapered central passageway 134. Such adhesive injection can be accomplished when the streamlined flexible strain relief 54 is mated to the distal end of the manifold 38 as shown in FIG. 6, or adhesive may be applied to the mated surfaces separately, or electronic welding or bonding can be incorporated, or adhesive may be otherwise suitably applied as applicable to the art.

The threaded high pressure connection port 60 is fitted and adhesively or otherwise suitably affixed to the interior of a high pressure connection branch passageway 124 of the high pressure connection branch 50. The threaded high pressure connection port 60 has a passageway 168 and is fitted to and adhesively or otherwise suitably affixed to the interior of the flangeless high pressure connection branch 50 of the manifold 18. Opposing flats 170 are located at the distal portion of the threaded high pressure connection port 60 to adequately receive adhesive 172 in close communication to ensure proper physical fixation and adhering of the threaded high pressure connection port 60 within the high pressure connection branch passageway 124 of the high pressure connection branch 50. An adhesive injection port 174 (FIG. 1) is located at a suitable location to extend through the high pressure connection branch 50 of the manifold 38 to introduce adhesive 172 to the interior region of the high pressure connection branch 50. The adhesive 172, in addition to adhering the flats 170 of the threaded high pressure connection port 60 to the high pressure connection branch passageway 124, also bonds the appropriate portions of the threads 62 of the threaded high pressure connection port 60 to the high pressure connection branch passageway 124. Adhesive injection can be accomplished when the threaded high pressure connection port 60 is mated to the high pressure connection branch 50 of the manifold 38, as shown in FIG. 6. Adhesive could also be applied to the mated surfaces separately, or electronic welding or bonding can be incorporated, or adhesive may be otherwise suitably applied as applicable to the art. Also shown is a ferrule 178 which aligns and suitably secures within the passageway 168 of the threaded high pressure connection port 60, the combination of which aligns partially within the high pressure connection branch passageway 124 of the high pressure connection branch 50.

One end of the high pressure tube 42 is utilized for delivery of high pressure ablation liquids and suitably secures in a center passage of the ferrule 178 to communicate with the passageway 168 of the threaded high pressure connection port 60. The high pressure tube 42 also extends through the high pressure connection branch passageway 124, through part of the tapered central passageway 134, through the streamlined flexible strain relief 54, through the capture catheter 40, and to the distal end of the capture catheter 40 to align within the retractable capture cone 56 where termination is provided in the form of a fluid jet emanator 180 (see FIGS. 1, 2 and 9).

Figure 7:
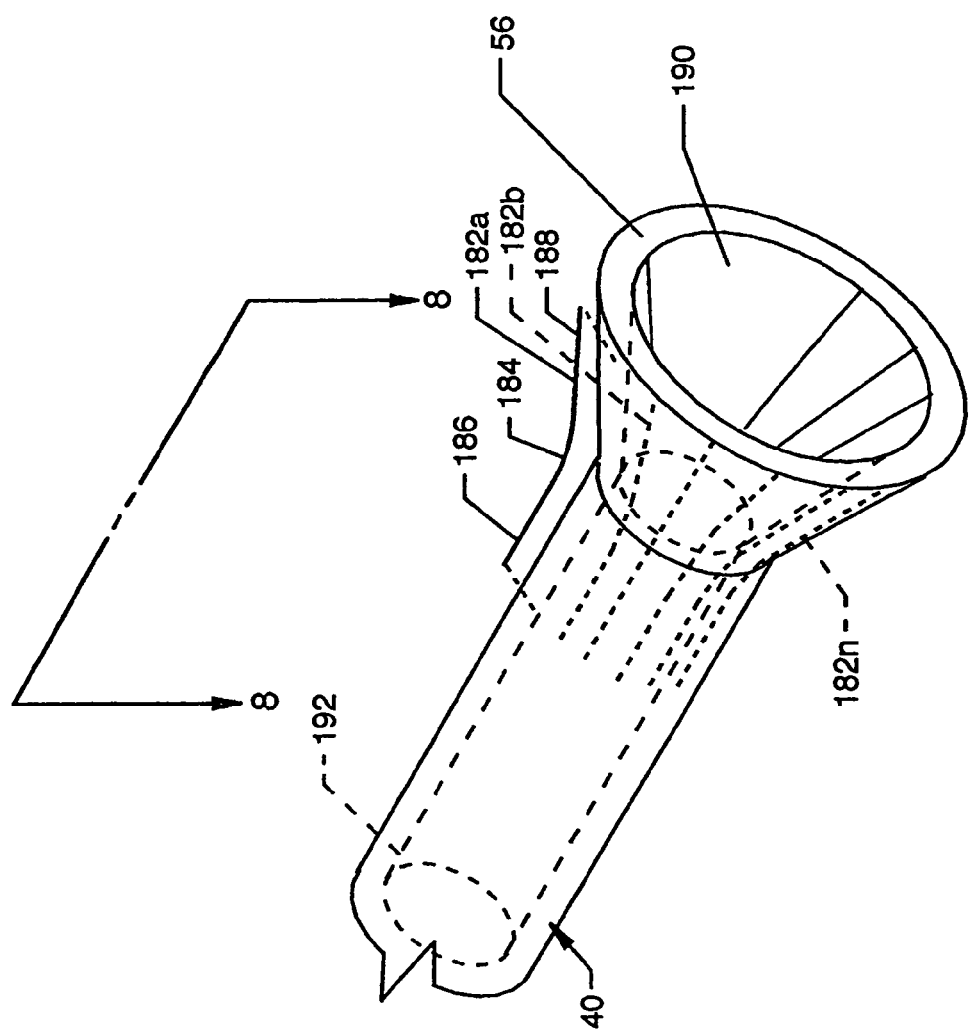
FIG. 7 is an isometric view showing the retractable capture cone in a deployed state at the distal end of a capture catheter.

FIG. 7 is an isometric view showing the retractable capture cone 56 in a deployed state at the distal end of the capture catheter 40. The retractable capture cone 56 and a portion of the capture catheter 40 can be a composition of materials including a plurality of expansion struts 182a–182n where, for illustration purposes, expansion strut 182a is shown distant from the structure of the deployed retractable capture cone 56. The expansion struts 182a–182n are preferably metallic or are of other such suitable material which can be formed to provide spring-like qualities having position memory in order to expandingly form the cone-like shape of the retractable capture cone 56. The expansion struts 182a–182n are encapsulated in polymers forming the capture catheter 40 and retractable capture cone 56 such as, but not limited to, PTFE, PEBAX, polyethylene, PET, polyamide, polyurethane or silicone. The expansion struts 182a–182n are preferably of metallic material such as, but not limited to, stainless steel, nitinol, nickel, platinum, iridium or tungsten. The expansion struts 182a–18n are preformed having a bend or curve 184 located between a straight strut portion 186 which resides generally in the non-cone-shaped distal region of the capture catheter 40 and a straight strut portion 188 directed at an angle from the first straight strut portion 186 and residing in the retractable capture cone 56. The interior conical surface 190 of the retractable capture cone 56 connects to and is in common with a lumen 192 extending the length of the capture catheter 40.

Figure 8:
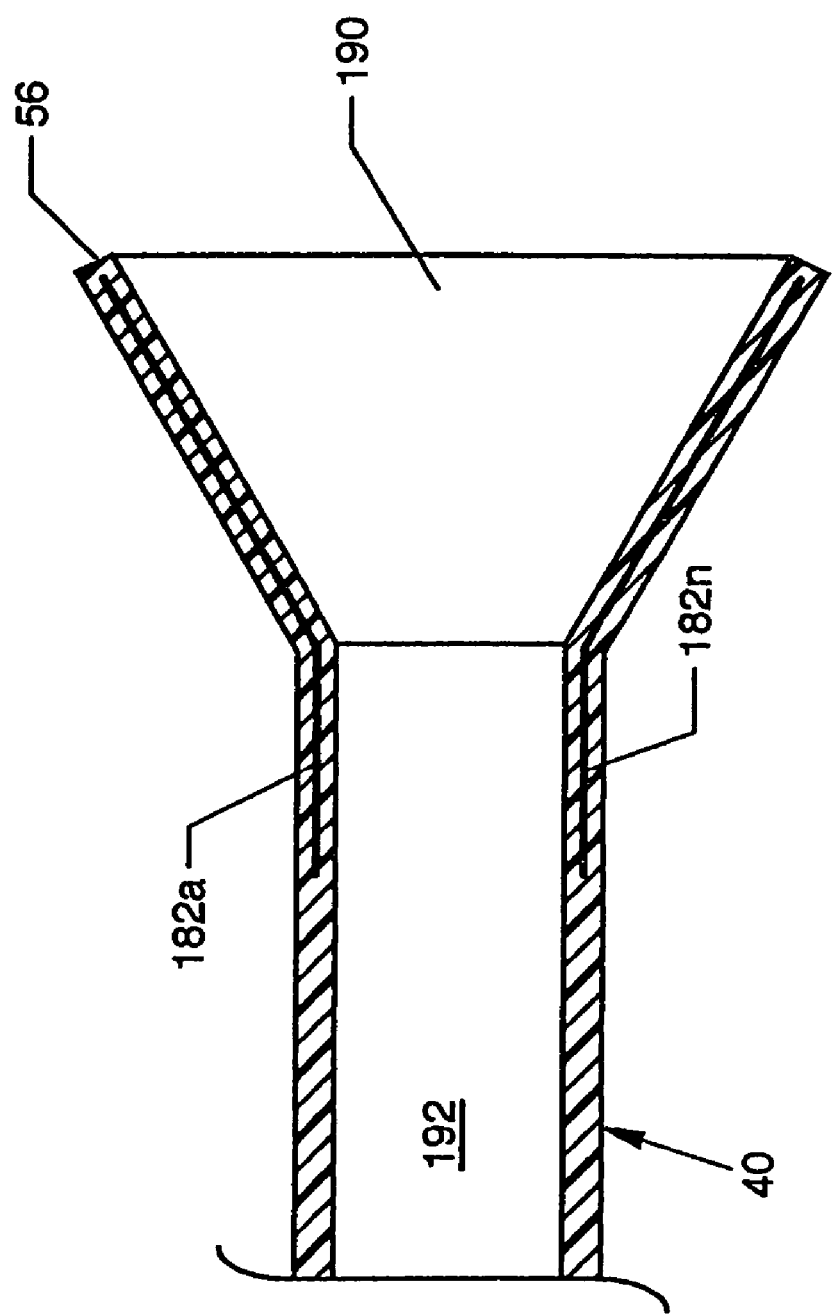
FIG. 8 is a cross section view along line 8—8 of FIG. 7 showing the retractable capture cone in a deployed state at the distal end of a capture catheter.

FIG. 8 is a cross section view of the retractable capture cone 56 along line 8—8 of FIG. 7 showing more clearly the expansion struts 182a–182n located within the retractable capture cone 56.

Figure 9:
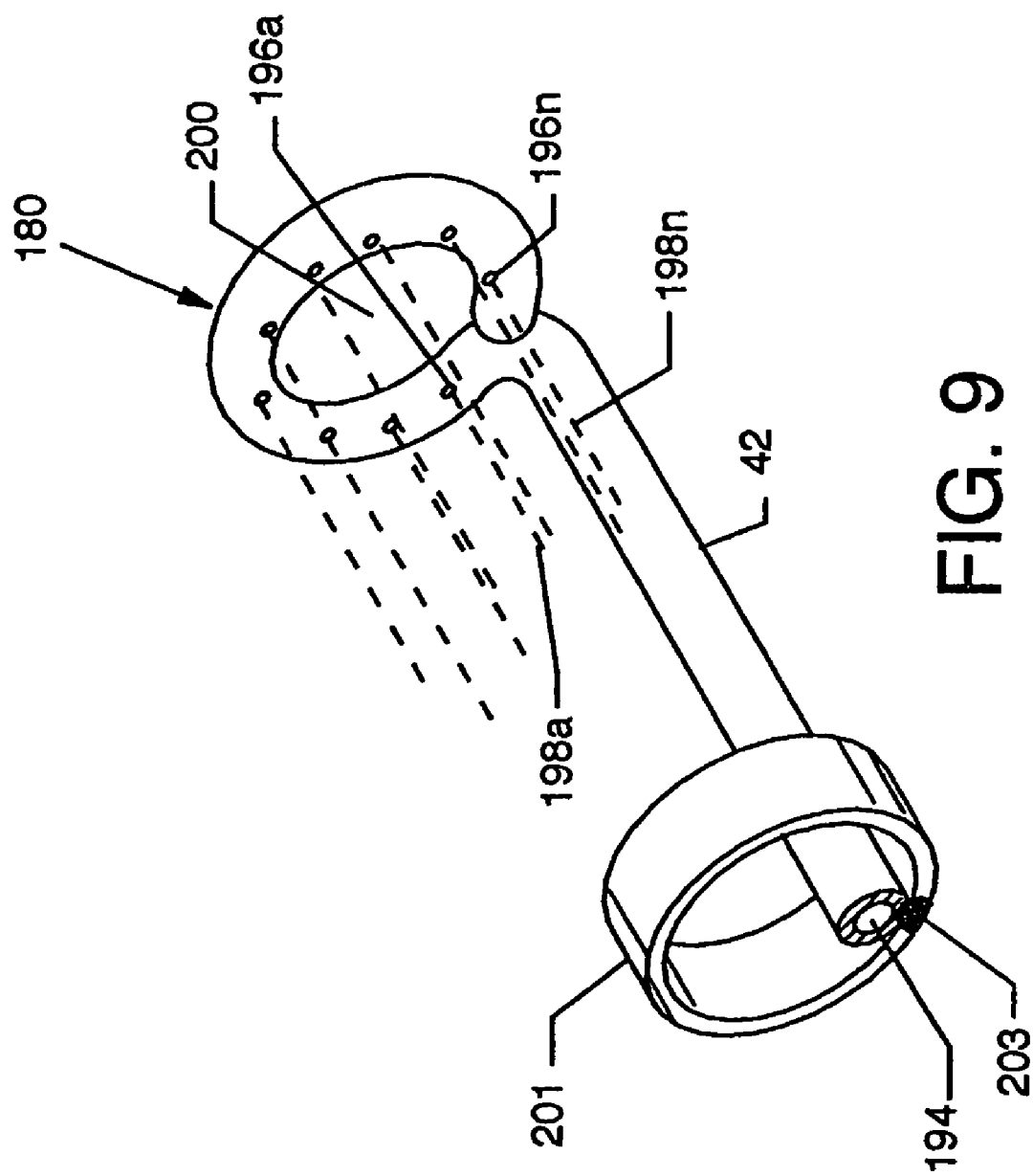
FIG. 9 is an isometric view of the fluid jet emanator located distally at one end of the high pressure tube.
Figure 10:
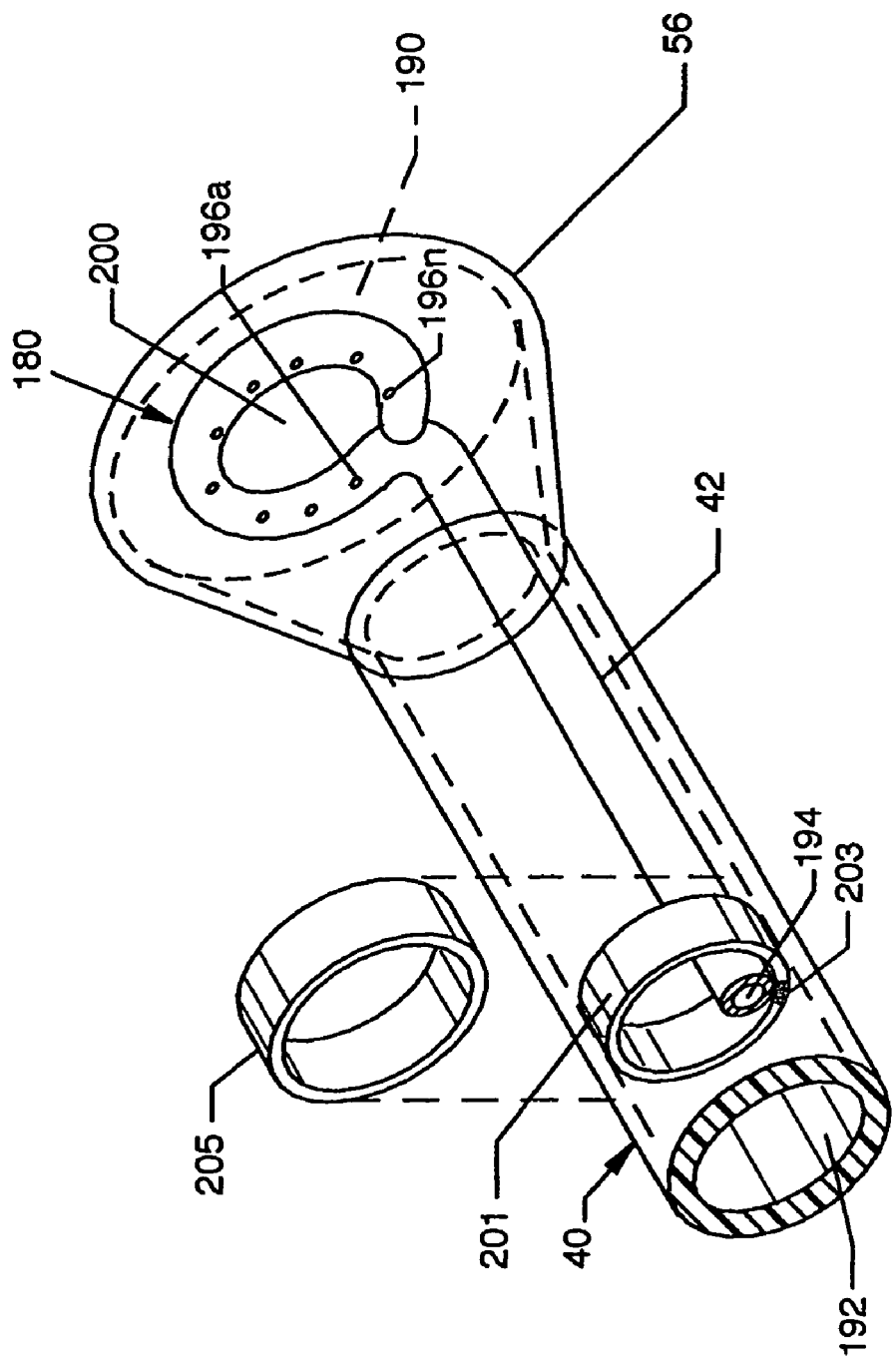
FIG. 10 is a transparent isometric view in partial cross section illustrating the alignment and attachment of the high pressure tube within the lumen of the capture catheter, which also favorably influences and provides for the alignment and fixed positioning of the fluid jet emanator with the retractable capture cone.

FIG. 9 is an isometric view of the fluid jet emanator 180 located distally at one end the high pressure tube 42. The fluid jet emanator 180 is a loop formed of the high pressure tube 42. A lumen 194 delivers high pressure saline or other such suitable fluid to the fluid jet emanator 180. A plurality of rearwardly and proximally directed jet orifices 196a–196n are located along the proximally facing portion of the fluid jet emanator 180. High pressure saline delivered by the lumen 194 is forced into the fluid jet emanator 180 to cause saline fluid jets 198a–198n to emanate from the rearwardly and proximally directed jet orifices 196a–196n. Such fluid jets 198a–198n are directed into the retractable capture cone 56 and are utilized to macerate, entrain and carry away thrombus, as later described in detail. The loop center 200 of the fluid jet emanator 180 accommodates passage of the occluder guidewire tube 32. A capture catheter support band 201 such as shown in this and alternate embodiments suitably attaches such as by a weld 203 to the high pressure tube 42 to maintain the position and orientation of the fluid jet emanator 180 with respect to the center of the support band 201 and also to the centerline of the capture catheter 42, as shown in FIG. 10. Although the fluid jet emanator 180 is shown as a loop formed of the high pressure tube 42, other suitably fashioned or shaped emanator designs can be utilized as an emanator and the use of the fluid jet emanator 180 having a loop shall not be considered to be limiting to the scope of the invention. For example, J-shaped, L-shaped, U-shaped, arcuate-shaped, semi-torodial-shaped, or other-shaped emanator(s) can be utilized. The emanator can have a single jet orifice from which a single fluid jet emanates, or a plurality of jet orifices from which a plurality of fluid jets emanate. The preferred configuration includes a plurality of proximally directed jet orifices.

FIG. 10 is a transparent isometric view in partial cross section illustrating the alignment and attachment of the high pressure tube 42 within the lumen 192 of the capture catheter 40, which also favorably influences and provides for the alignment and fixed positioning of the fluid jet emanator 180 with the retractable capture cone 56. Such fixed positioning and alignment is provided by the capture catheter support band 201 being fixedly aligned within the lumen 192 of the capture catheter 40. The capture catheter support band 201 is positionally fixed within the lumen 192 by frictional engagement of a cylindrically shaped radiopaque marker band 205, such as shown in this and alternate embodiments, engaged over and about the capture catheter 40.

Figure 11:
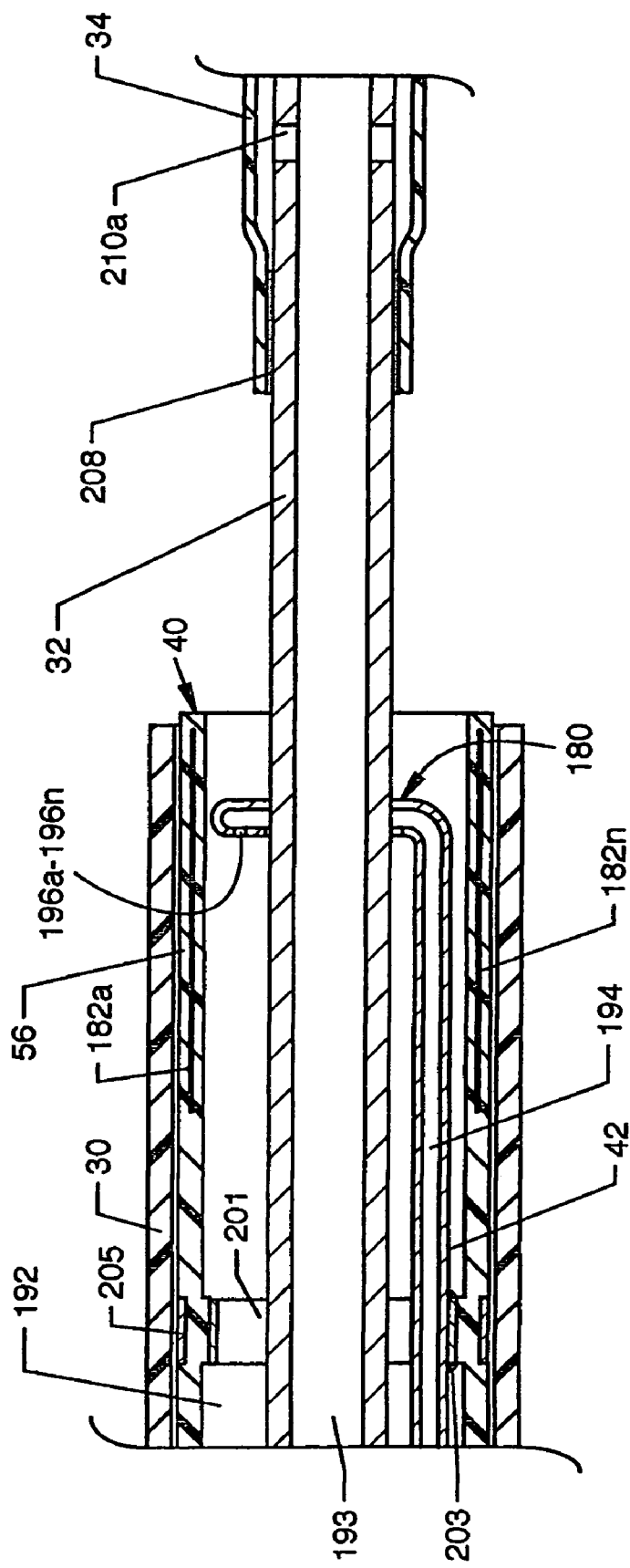
FIG. 11 is a longitudinal cross sectional view of the distal region of the capture catheter including the collapsed retractable capture cone, and the fluid jet emanator aligned over the occluder guidewire tube in the distal region of the guide catheter.

FIG. 11 is a longitudinal cross section view of the distal region of the capture catheter 40 including the collapsed retractable capture cone 56, and the fluid jet emanator 180 aligned in the distal region of the capture catheter 40 prior to deployment of the retractable capture cone 56. Also shown is the occluder guidewire tube 32 aligned within the lumen 192 of the capture catheter 40. Also shown is the guide catheter 30 in which the capture catheter 40 aligns.

Figure 12:
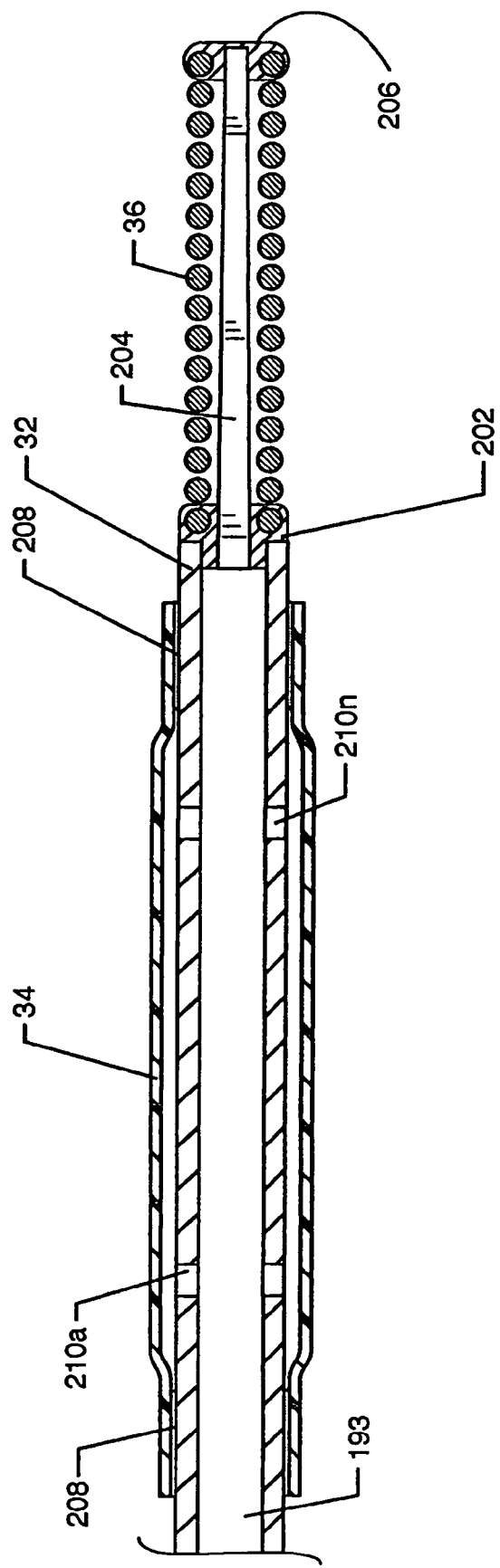
FIG. 12 is a longitudinal cross sectional view of the distal region of the occluder guidewire tube.

FIG. 12 is a longitudinal cross sectional view of the distal region of the occluder guidewire tube 32. Shown in particular is a weld 202 which joins together the extreme distal portion of the occluder guidewire tube 32, the proximal end of the guidewire coil 36, and the proximal end of a tapered flexible core 204. A weld 206 is also included at the distal end of the guidewire coil 36 to secure the distal end of the tapered flexible core 204 to the distal end of the guidewire coil 36 and to provide for smooth entry into a vessel or body cavity device orifice. The balloon occluder 34 aligns around and about the distal portion of the occluder guidewire tube 32 and the distal and proximal ends of the balloon occluder 34 secure by adhesive 208 or other suitable attachment means to the periphery of the occluder guidewire tube 32. Such securing seals the balloon occluder 34 to the periphery of the occluder guidewire tube 32 to allow sustained inflation of the balloon occluder 34 by pressurizing the lumen 193 with a medium such as liquid or gas whereby such pressurizing medium is delivered through a plurality of inflation orifices 210a–210n located around and about the distal portion of the occluder guidewire tube 32. Alternatively, a single inflation orifice can be used, although this is not the preferred configuration.

MODE OF OPERATION

FIGS. 1 and 13–17 illustrate the mode of operation of the thrombectomy catheter system with occluder 10 and the method of using the same. FIG. 1 shows the thrombectomy catheter system with occluder 10 in use with supporting operational sources including, but not limited to, a balloon inflation source 12, a high pressure source 14, and a suction source 16. Fluoroscopy is incorporated to monitor the position of the invasive components of the system in the region of thrombus residing in the vasculature.

Figure 13:
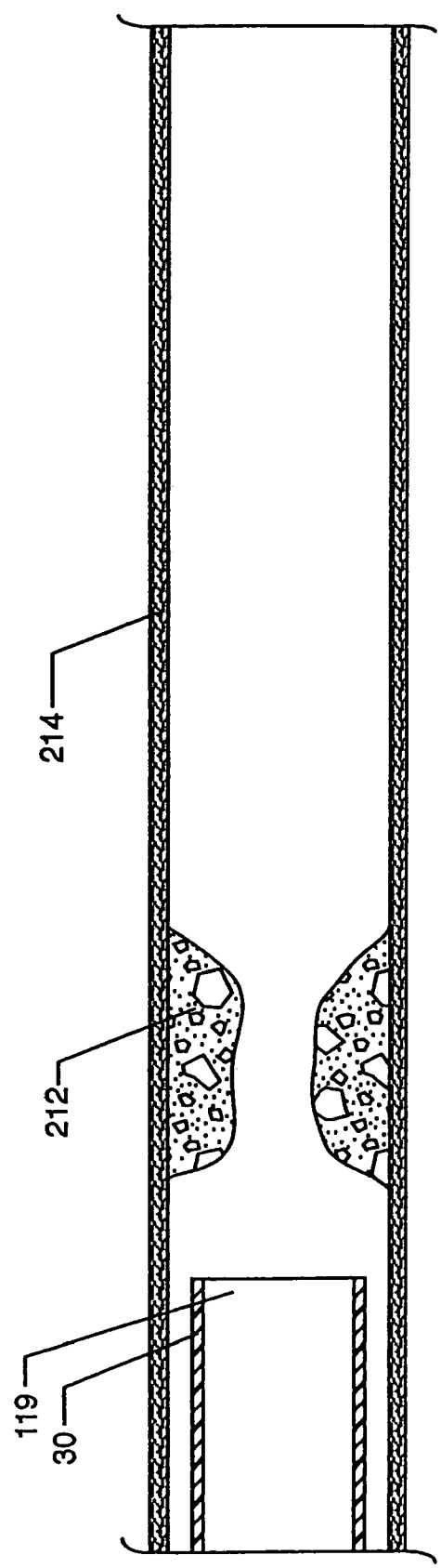
FIG. 13 is a longitudinal cross sectional view showing the distal end of the guide catheter advanced into a blood vessel to a position just proximal of a buildup of thrombus or other undesirable embolic materials.

As shown in FIG. 13, the distal end of the guide catheter 30 is advanced into a blood vessel 214 or other vessel to a position just proximal of a buildup of thrombus 212 or other undesirable embolic materials. Such advancement involves the manipulation of the manifold 18 to which the guide catheter 30 is attached.

Figure 14:
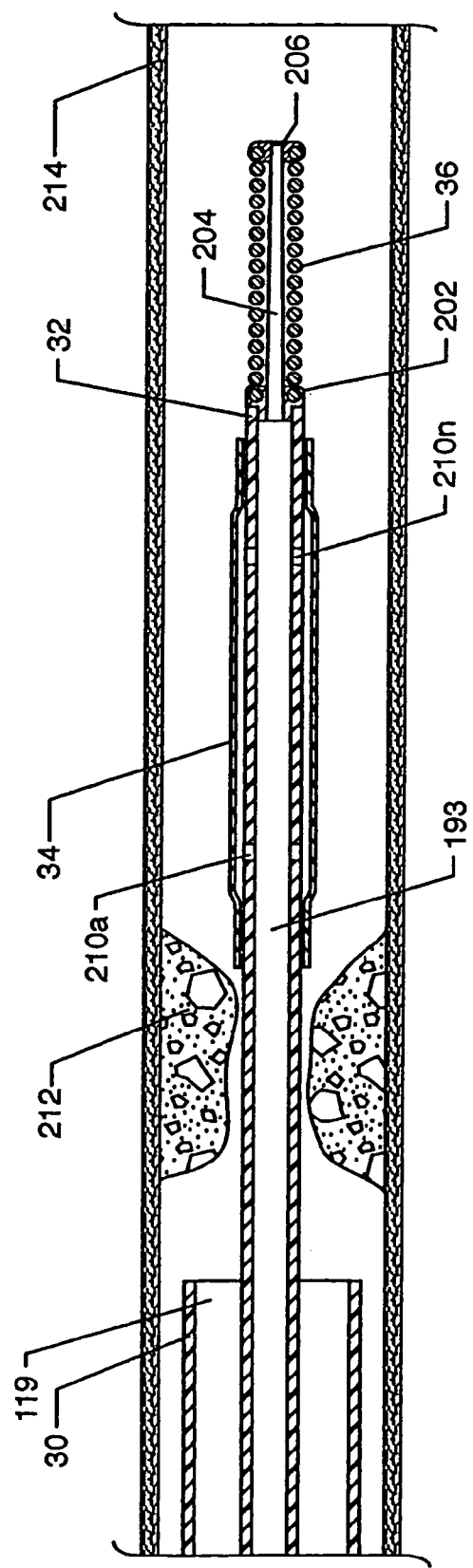
FIG. 14 is a longitudinal cross sectional view showing the distal end of the occluder guidewire tube, including the guidewire coil and an occluder in the form a balloon, advanced through and beyond a thrombus site in a blood vessel and showing the distal end of the guide catheter just proximal of the thrombus site.

The distal end of the occluder guidewire tube 32 is then loaded through the hemostasis nut 20 and into and through the manifold 18 and thence through the lumen 119 of the guide catheter 30 and advanced beyond the distal end of the guide catheter 30. The distal end of the occluder guidewire tube 32, including the guidewire coil 36 and the balloon occluder 34, is advanced through and beyond the thrombus 212, as shown in FIG. 14, whereby the proximal end of the balloon occluder 34 is positioned just distal of the thrombus 212. The proximal end of the occluder guidewire tube 32 of suitable length is left extending a suitable distance beyond the proximal end of the hemostasis nut 20 for accommodation of the capture catheter 40 and various associated components of the manifold 38 attached thereto.

Figure 15:
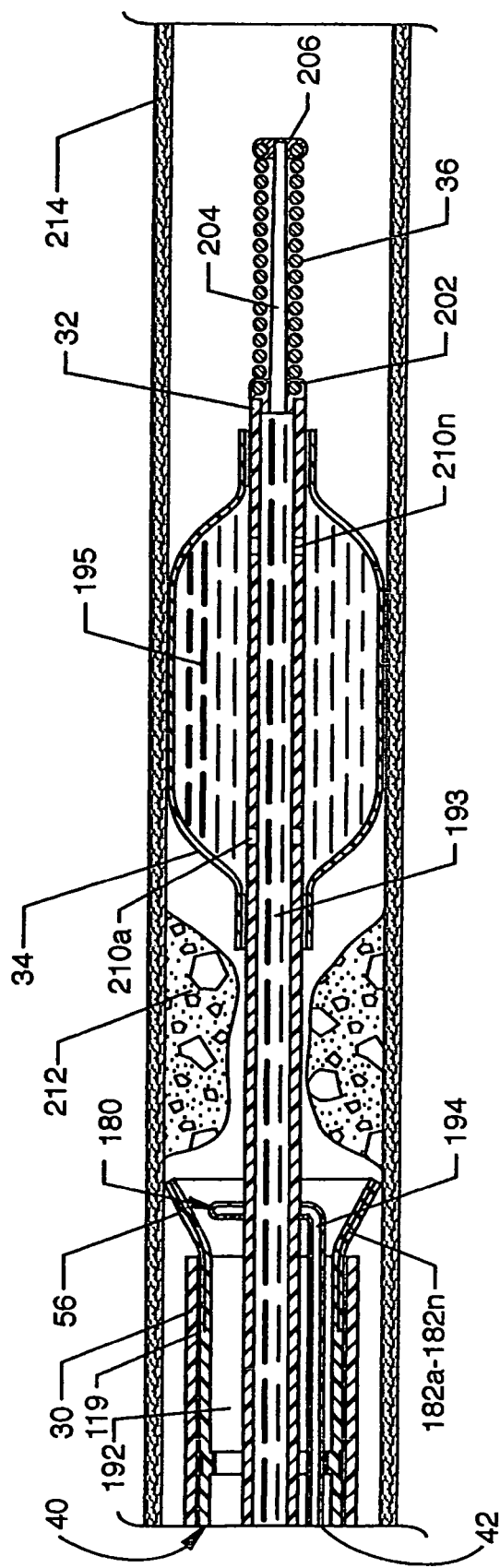
FIG. 15 is a longitudinal cross sectional view showing elements of the thrombectomy catheter system with occluder within a blood vessel and showing saline or other suitable medium as provided by a balloon inflation source to pressurize the lumen of the occluder guidewire tube and to deliver pressurized saline through the plurality of inflation orifices to inflate and expand the balloon occluder to occlude the blood vessel.

The distal end of the capture catheter 40, including the retractable capture cone 56 and the fluid jet emanator 180, is then loaded over the proximal end of the occluder guidewire tube 32 where the lumen 192 of the capture catheter 40 and the loop center 200 of the fluid jet emanator 180 accommodate the occluder guidewire tube 32. Saline or other suitable medium as provided by the balloon inflation source 12 pressurizes the lumen 193 of the occluder guidewire tube 32 to deliver pressurized saline 195 through the plurality of inflation orifices 210a–210n to inflate and expand the balloon occluder 34 to occlude the blood vessel 214, as shown in FIG. 15. The manifold 38 is then maneuvered to ensure full and proper positioning of the capture catheter 40 and especially the retractable capture cone 56 with respect to the distal end of the guide catheter 30 and the thrombus 212, as shown in FIG. 15. The retractable capture cone 56, when positioned suitably beyond the distal end of the guide catheter 30, expands with the aid of the expansion struts 182a–182n to a cone shape to contact the inner periphery of the blood vessel 214. When the balloon occluder 34 is inflated and when the retractable capture cone 56 is fully deployed, each against the wall of the blood vessel 214, maceration and removal of thrombus 212 is then commenced, as shown in and as described with reference to FIGS. 16 and 17.

Figure 16:
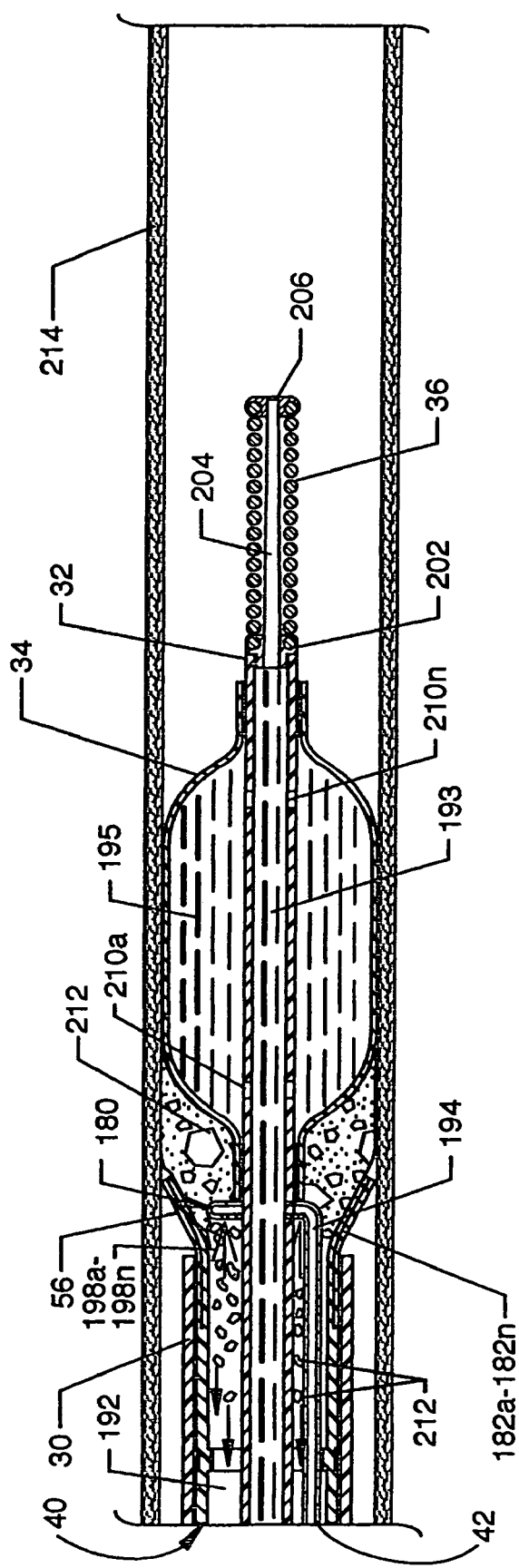
FIG. 16 is a view like FIG. 15 but showing the inflated balloon occluder impinging and urging thrombotic deposits for fluid jet impingement at the retractable capture cone.

As shown in FIG. 16, high pressure medium such as high pressure saline such as provided by the high pressure source 14 is delivered by the lumen 194 of the high pressure tube 42 and forced into the fluid jet emanator 180 to cause rearwardly directed saline fluid jets 198a–198n (also seen in FIG. 9) to emanate from the rearwardly directed jet orifices 196a–196n. Such fluid jets 198a–198n are directed into the retractable capture cone 56 and are utilized to macerate, entrain and carry away thrombus 212, the delivery of which is caused by the proximal urging of the inflated balloon occluder 34. Proximally directed urging of the thrombus 212 by the inflated balloon occluder 34 is facilitated by manipulation of the manifold 38 which, being connected to and in direct communication with the occluder guidewire tube 32 and attached inflated balloon occluder 34, impinges, dislodges, reshapes and redistributes the thrombus 212 in a proximal direction for subsequent interaction with the rearwardly directed saline fluid jets 198a–198n. Proximally urged thrombus 212 is forced by the proximally directed balloon occluder 34 into the deployed retractable capture cone 56 proximally towards, about and around the fluid jet emanator 180 where the proximally directed fluid jets 198a–198n impinge, dislodge, macerate, reduce and otherwise influence the shape and structure of the thrombus 212 for evacuation. Suction appropriately applied to the lumen 192 of the capture catheter 40, such as by the suction source 16, creates a low pressure which, along with the rearwardly directed fluid jets 198a–198n, carries the macerated thrombus 212 proximally for collection at the suction source 16.

Figure 17:
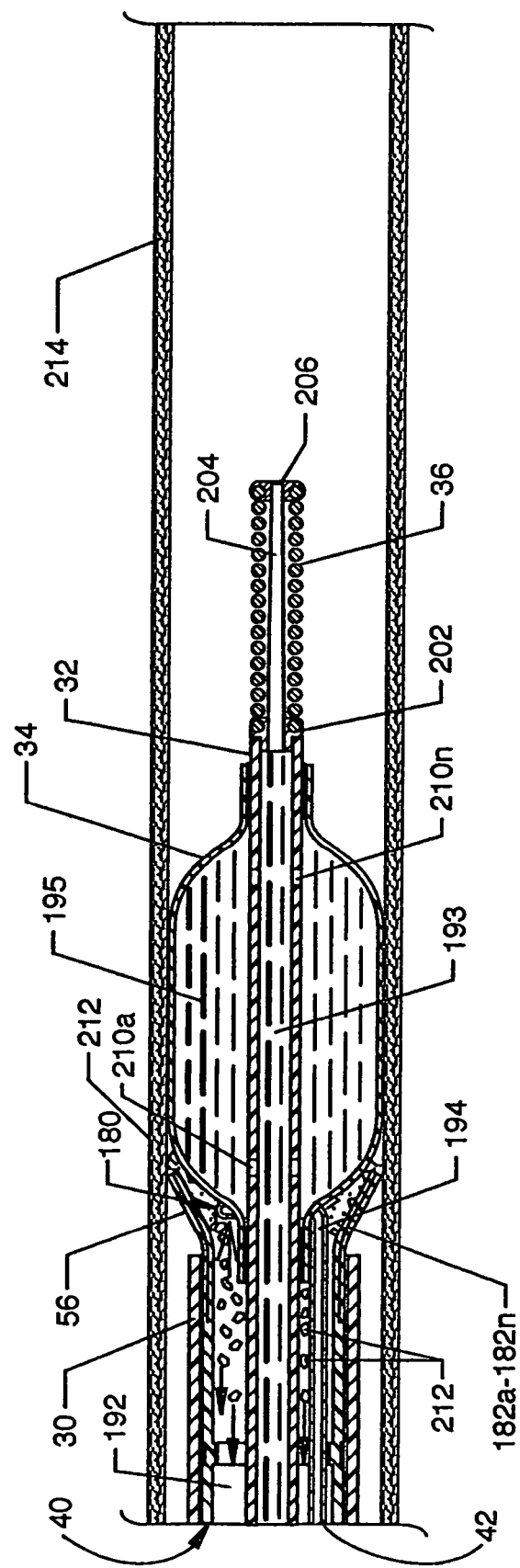
FIG. 17 is a view like FIG. 16 but showing the inflated balloon occluder near impingement with the retractable capture cone where the majority of the thrombus has been macerated at the retractable capture cone and evacuated through the lumen of the capture catheter.

FIG. 17 shows the inflated balloon occluder 34 near impingement with the retractable capture cone 56 where the majority of the thrombus 212 has been macerated at the retractable capture cone 56 and evacuated through the lumen 192 of the capture catheter 40. Subsequent to removal of thrombus 212, the balloon occluder 34 can be deflated and collapsed to the same size or smaller size than the capture catheter 40 such as by relieving or even applying negative pressure at the balloon inflation source 12. Such reduction in size of the balloon occluder 34 allows manipulation of the occluder guidewire tube 32 proximally to retract the collapsed balloon occluder 34 into the capture catheter 40. Once the collapsed balloon occluder 34 is contained inside the confines of the capture catheter 40, the capture catheter 40 can be retracted proximally to retractably collapse the retractable capture cone 56 to conform to the inner regions of the guide catheter 30 whereupon the capture catheter 40 and the occluder guidewire tube 32 can be withdrawn simultaneously, if desired. Alternatively, the guide catheter 30, the capture catheter 40 and the occluder guidewire tube 32 could be advanced distally as required to facilitate the removal of other thrombus as required.

Many of the following alternative embodiments and illustrations include originally shown and described elements of the invention. Alternative versions of first embodiment elements may include reference numerals having suffixes where the numeral relates to a previously described invention element of an element and the addition of a suffix, except for element pluralities, indicates that an alternate version of an element is shown and utilized.

Figure 18:
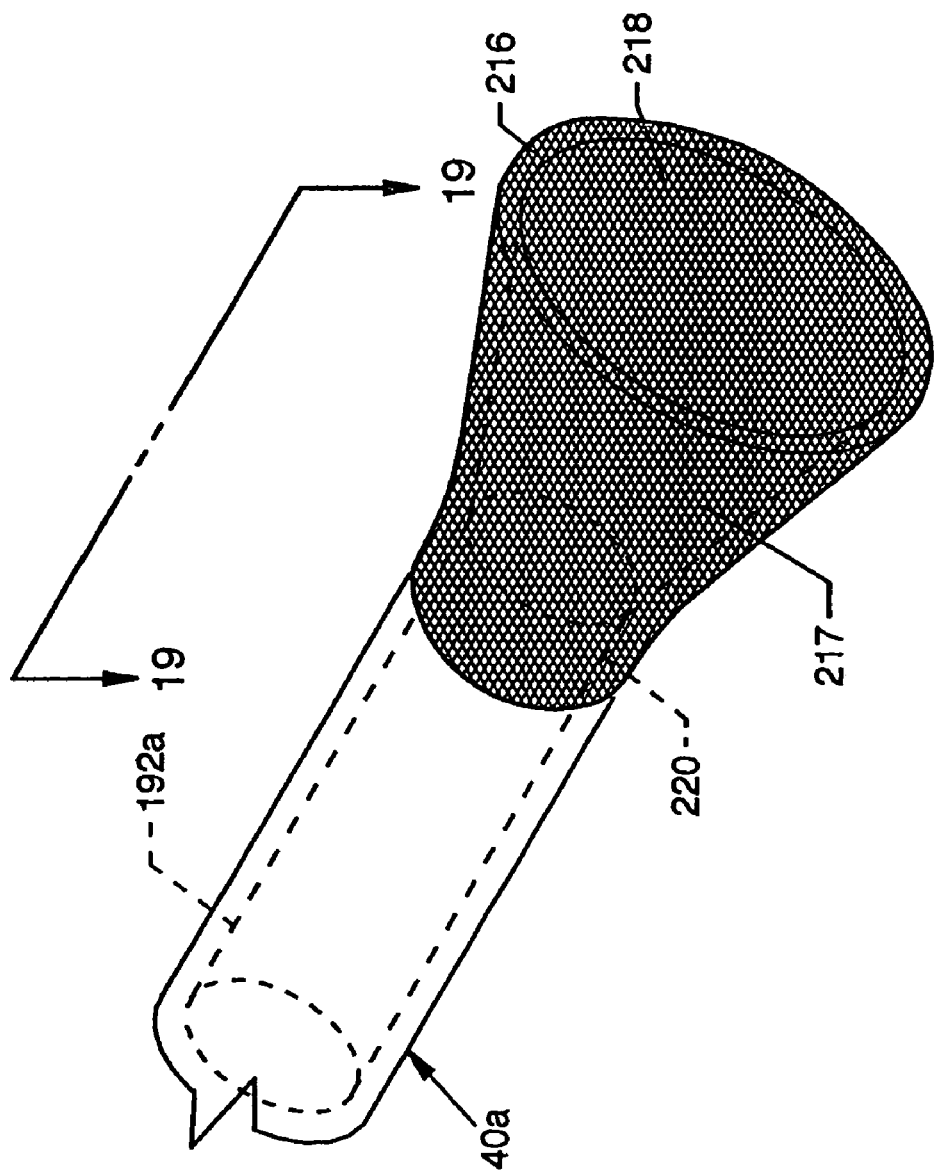
FIG. 18, an alternative embodiment, illustrates a retractable capture cone of flexible plastic mesh formed by weaving, braiding, or other such interlacing of strands, filaments or the like having position memory in a deployed state at the distal end of a capture catheter.

FIG. 18 is an alternative embodiment where the retractable capture cone 56 and expansion struts 182a–182n previously described are replaced by a retractable capture cone 216 preferably of flexible plastic mesh 217 formed by weaving, braiding, or other such interlacing of strands, filaments or the like, preferably of Nitinol, or other materials such as nylon or polyurethane, or metallic or other non-metallic flexible materials all having position memory. The retractable capture cone 216 functions much the same as the retractable capture cone 56 whereby the retractable capture cone 216 can conformingly assume a cylindrical shape when residing adjacent to, in alignment with, and in communication with a lumen 192a of a capture catheter 40a where such capture catheter 40a replaces and is like capture catheter 40 but includes a distal annular recess 220 for accommodation and suitable attachment, such as by, but not limited to, adhesive 219 (FIG. 19), depending on the material used, of the proximal end of the retractable capture cone 216. The retractable capture cone 216 because of positional memory can expand outwardly to form a conical or other suitable useful shape which can contact the inner periphery of the blood vessel 214. The retractable capture cone 216 is of close-knit material, such as described above, which does not allow fluids to pass therethrough and which functions in a somewhat identical manner to the retractable capture cone 56 where a conical surface 218 on the inside of the retractable capture cone 216 functions to channel thrombus 212 and receive fluid jets 198a–198n for thrombus maceration and subsequent thrombus evacuation through the lumen 192a of the capture catheter 40a according to the teachings of the invention.

Figure 19:
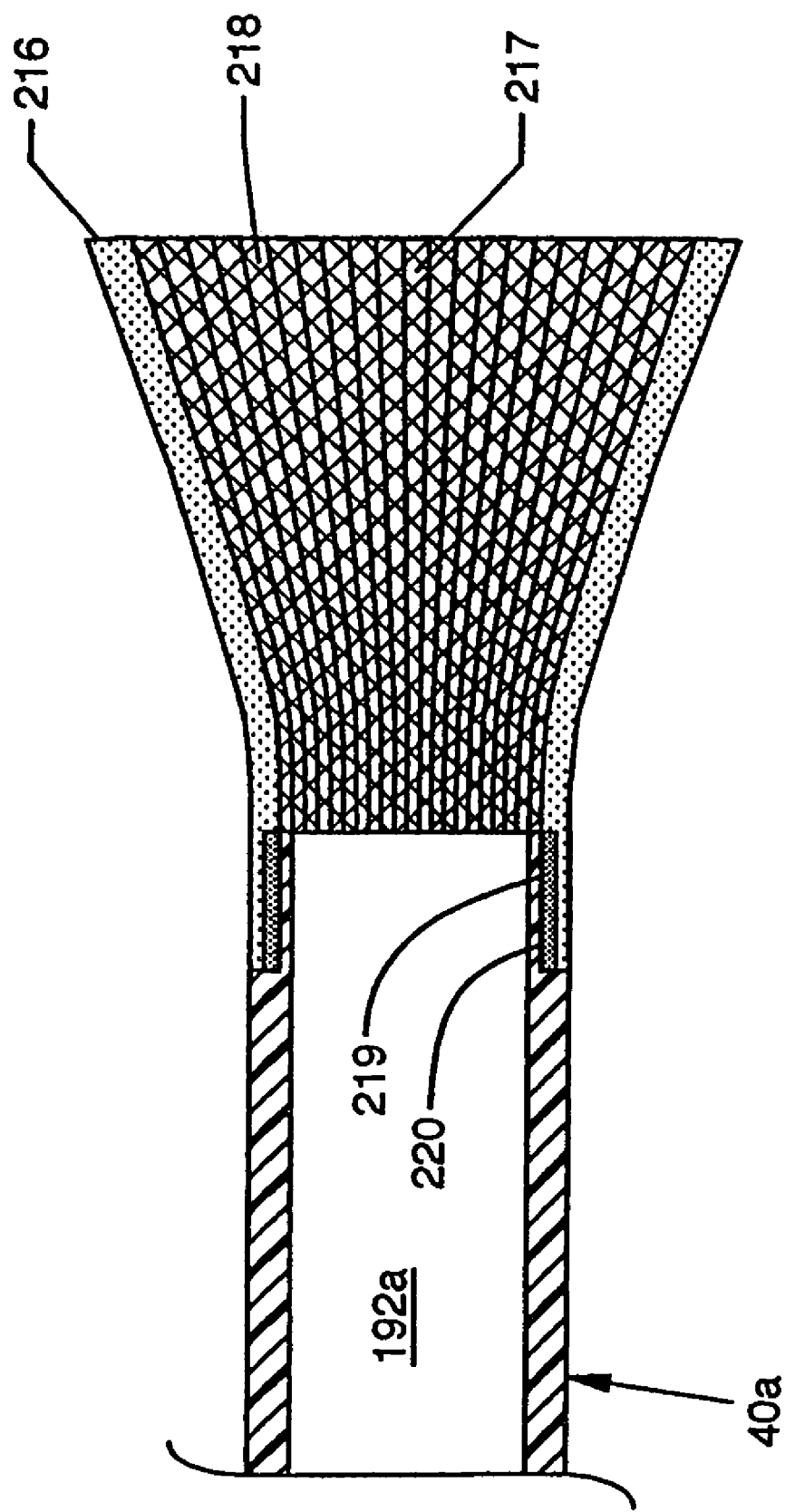
FIG. 19 is a cross section view of the capture catheter and retractable capture cone along line 19—19 of FIG. 18.

FIG. 19 is a cross section view of the capture catheter 40a and retractable capture cone 216 along line 19—19 of FIG. 18. Shown in particular is the annular recess 220 which accommodates the proximal end of the retractable catheter cone 216 and which accommodates a suitable attachment medium such as an adhesive 219, or, alternatively, weldments or other attachment means. The annular recess 220 provides for attachment of the retractable capture cone 216 having no protrusions or irregular surfaces which can interfere with smooth unencumbered passage of the union of the capture catheter 40a and the retractable capture cone 216 at the distal tip of the guide catheter 30.

Figure 20:
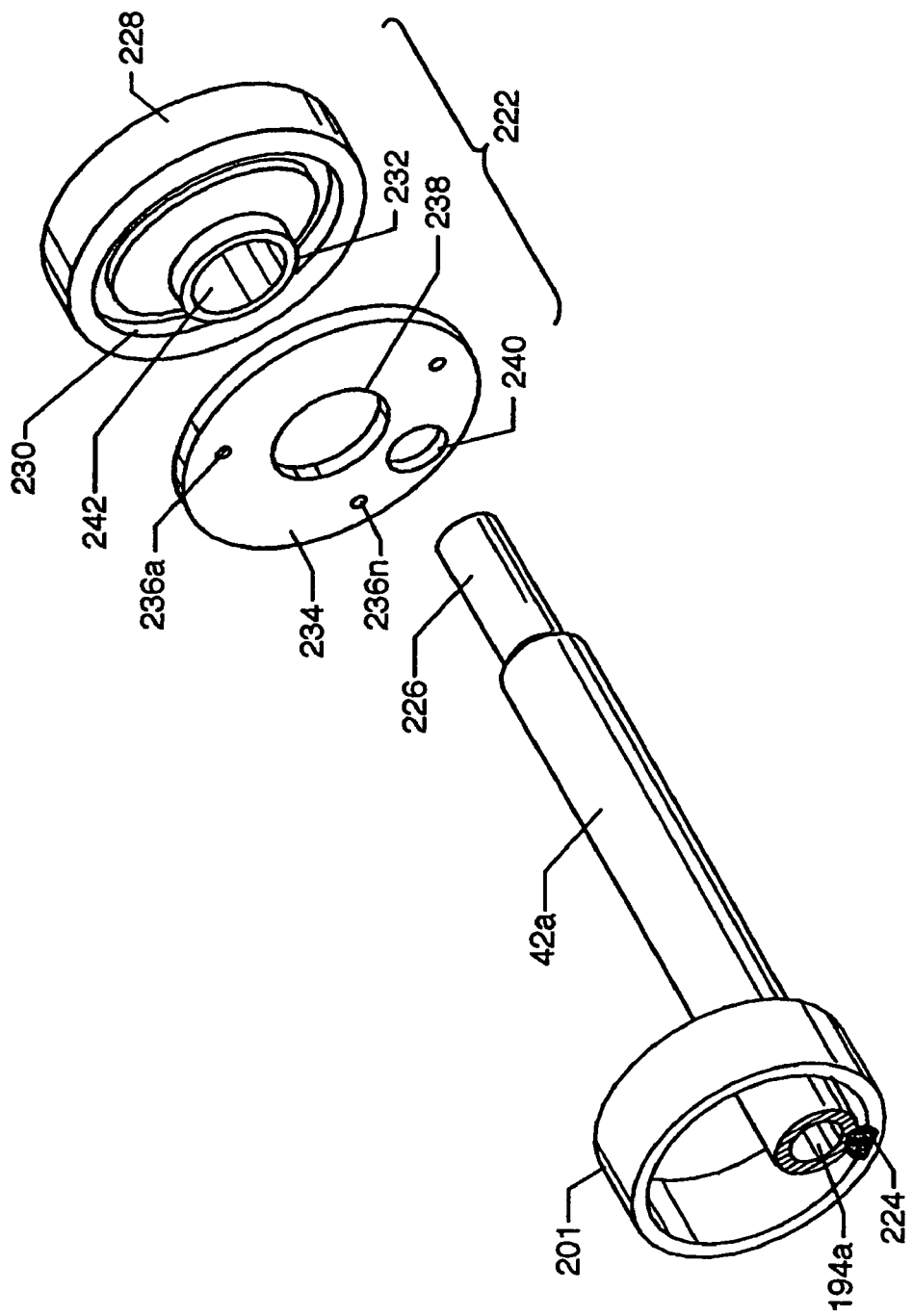
FIG. 20, an alternate embodiment, is an exploded isometric view depicting an alternative fluid jet emanator and the relationship of the capture catheter support band to a high pressure tube.
Figure 21:
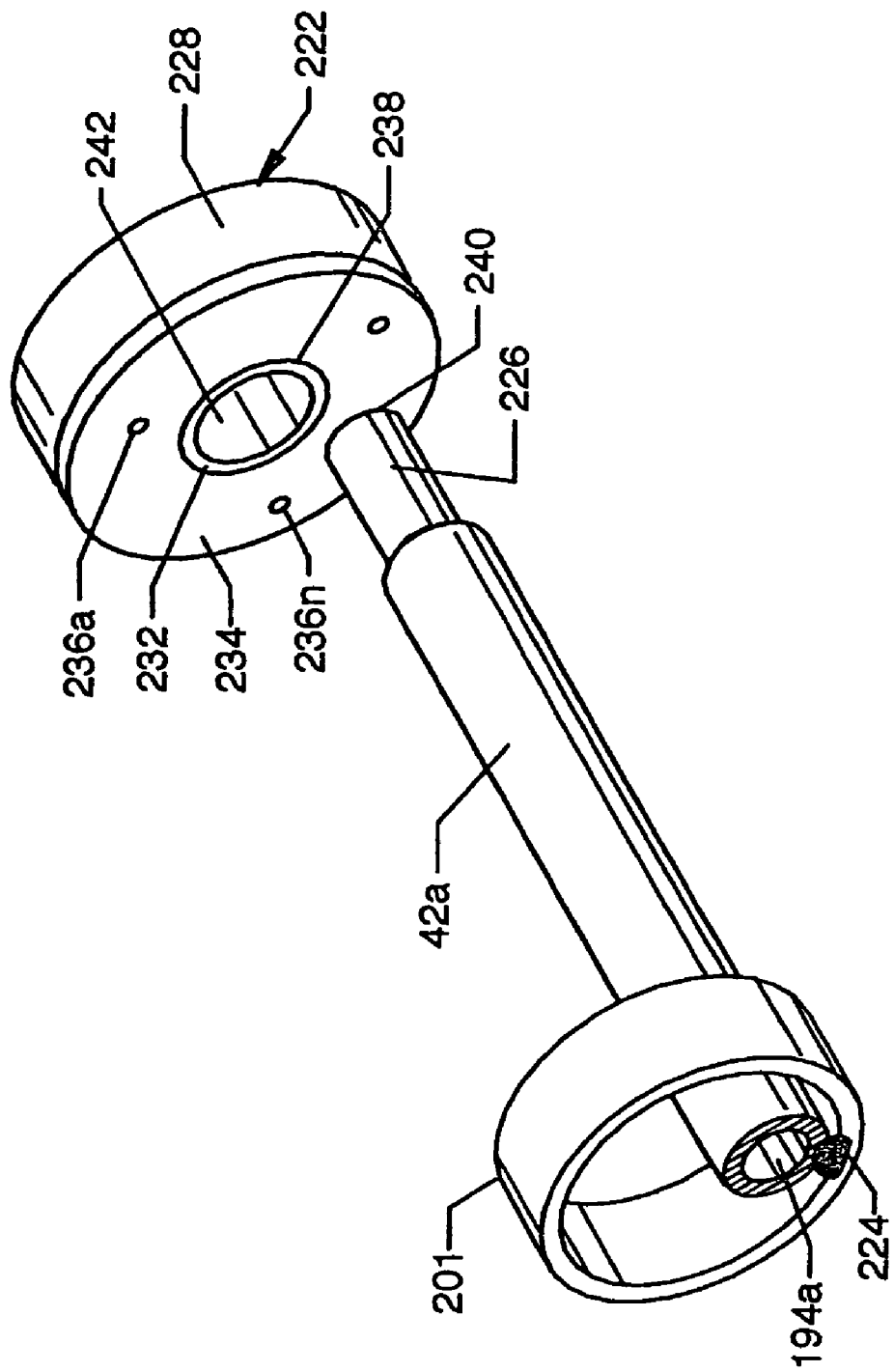
FIG. 21 is an assembled isometric view of the elements of FIG. 20.
Figure 22:
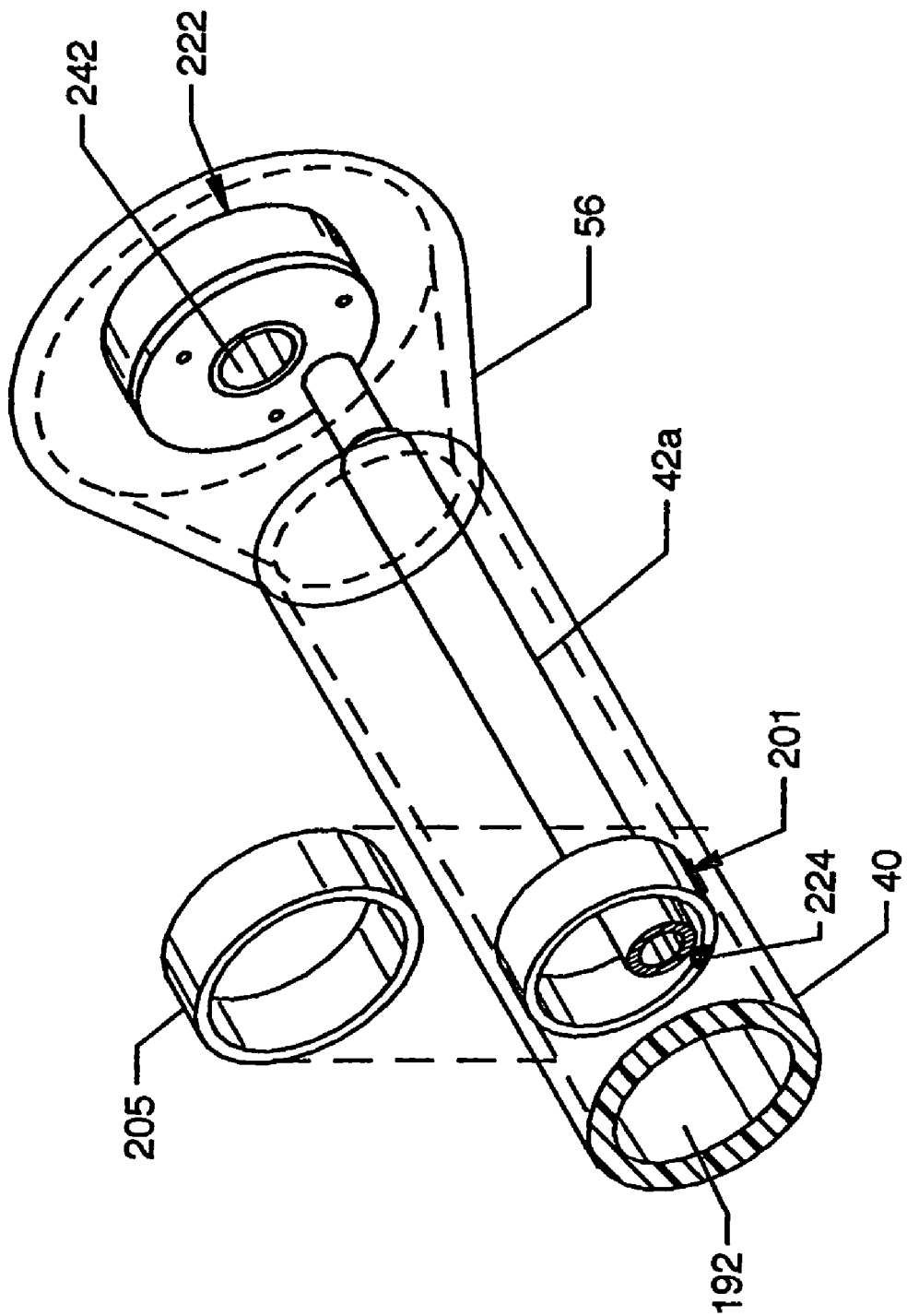
FIG. 22 is a transparent isometric view of the elements of FIGS. 20 and 21 in partial cross section illustrating the alignment and attachment of the high pressure tube within a lumen of a capture catheter.

FIGS. 20, 21 and 22 illustrate an alternative embodiment fluid jet emanator 222 which can be utilized in lieu of the previously described fluid jet emanator 180. FIG. 20 is an exploded isometric view depicting the alternative fluid jet emanator 222 and the relationship of the capture catheter support band 201 to a high pressure tube 42a. FIG. 21 is an assembled isometric view of the elements of FIG. 20; and FIG. 22 is a transparent isometric view of the elements of FIGS. 20 and 21 in partial cross section illustrating the alignment and attachment of the high pressure tube 42a within the lumen 192 of the capture catheter 40 which also favorably influences and provides for the alignment and fixed positioning of the fluid jet emanator 222 with the retractable capture cone 56. Such fixed positioning and alignment is provided by the capture catheter support band 201 being fixedly aligned within the lumen 192 of the capture catheter 40. The capture catheter support band 201 secures such as by a weld 224 or other suitable attachment means to the lower surface of the high pressure tube 42a. The capture catheter support band 201 is fixed at a suitable position along the interior (lumen 192) of the capture catheter 40 by the compressional frictional engagement of a radiopaque marker band 205 over and about the capture catheter 40, as shown in FIG. 22.

The high pressure tube 42a is reduced in diameter at the high pressure tube 42a distal end 226 for suitable engagement with the fluid jet emanator 222. The fluid jet emanator 222 is built as a structure outwardly resembling the general shape of a disk. The fluid jet emanator 222 includes a cylindrical main body 228, an annular manifold groove 230 in the form of a circular groove at the proximal end of the cylindrical main body 228, a centrally located tubular extension 232 extending proximally from the proximal end of the main body 228 and being coaxial with the annular manifold groove 230, a manifold plate 234 aligned to the annular manifold groove 230 and the adjacent planar annular surfaces having a plurality of jet orifices 236a–236n, a centrally located hole 238, and an offset hole 240. The centrally located hole 238 is aligned to and accommodated by the tubular extension 232. The manifold plate 234 is also aligned substantially to the proximal end of the main body 228 during the mating of the centrally located hole 238 and the tubular extension 232. A passageway 242 aligns to the longitudinal axis of the main body 228, the center of the tubular extension 232 and to the center of the centrally located hole 238 of the manifold plate 234. An annular manifold is formed when the manifold plate 234 is mated over and about the annular manifold groove 230 of the main body 228, at which time the plurality of jet orifices 236a–236n and the offset hole 240 are brought into close communicational sealed alignment with the annular manifold groove 230 in the main body 228.

High pressure fluid such as saline or other suitable solution is delivered through the lumen 194a of the high pressure tube 42a to the fluid jet emanator 222 and distributed through the formed manifold to the plurality of jet orifices 236a–236n, whereby high velocity jet flow emanates proximally for maceration of thrombus delivered to the retractable capture cone 56 by the balloon occluder 34 or other suitably fashioned structure described herein for subsequent evacuation through the capture catheter 40.

The radiopaque marker band 205 positions near and over and about the distal end of the capture catheter 40 for engagement of the capture catheter 40 by compressional frictional engagement and causes the capture catheter 40 to frictionally engage the capture catheter support band 201, as shown in FIG. 22. In the alternative, the capture catheter 40a and the mesh style retractable capture cone 216 previously described could be incorporated in lieu of the capture catheter 40 and the retractable capture cone 56 shown in FIG. 22.

Figure 23:
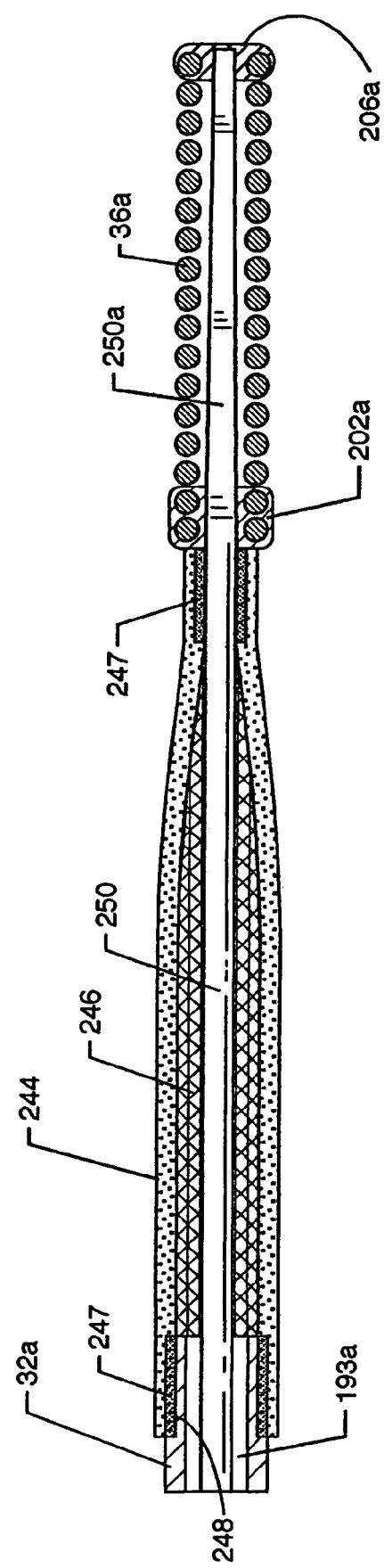
FIG. 23 is a cross section view of an alternative embodiment incorporating a controllable-shape mesh occluder.

FIG. 23 is a cross section view of an alternative embodiment incorporating a controllable-shape mesh occluder 244 having structure providing a shape when expanded and distended substantially similar to and performing the same thrombotic influencing function as the previously described inflated balloon occluder 34. The controllable-shape mesh occluder 244 is not inflatable but has a shape which is controllable and which is distendingly expandable. The controllable-shape mesh occluder 244 is fabricated of flexible mesh 246, which can be a braid, a weave, or other interlacing strands or the like of metallic or non-metallic flexible materials, which optionally can include positional memory. The flexible mesh 246 is of close-knit material, such as described above, which does not allow fluids to pass therethrough. The controllable-shape mesh occluder 244 and the occluder guidewire tube 32a can be utilized in lieu of the balloon occluder 34 and the occluder guidewire tube 32 previously described according to the teachings of the invention where the controllable-shape mesh occluder 244 is positioned and expandingly deployed to assume a shape generally resembling the balloon occluder 34.

The occluder guidewire tube 32a, having a lumen 193a, replaces and is like the occluder guidewire tube 32, but includes a distal annular recess 248 for accommodation and suitable attachment thereto, such as by, but not limited to, adhesive 247, depending on the material used, of the proximal end of the flexible mesh 246 which forms the controllable-shape mesh occluder 244. A control rod 250 extends in the lumen 193a the length of the occluder guidewire tube 32a to exit the occluder guidewire tube 32a at the proximal end of the occluder guidewire tube 32a and to extend beyond so that the physician operator may adjustably control the control rod 250. The distal portion of the control rod 250 which extends beyond the distal end of the controllable-shape mesh occluder 244 has the shape and characteristics of the tip of any ordinary coronary guidewire of the previously shown tapered flexible core 204 to form a tapered flexible core 250a. A weld 202a attaches the proximal end of a guidewire coil 36a to the proximal end of the tapered flexible core 250a, and a weld 206a attaches the distal end of the guidewire coil 36a to the distal end of the tapered flexible core 250a. In the alternative, the control rod 250 and the tapered flexible core 250a could be separate elements mutually joined with the guidewire coil 36a at weld 202a. The distal end of the controllable-shape mesh occluder 244 suitably attaches, such as by use of adhesive 247 or other suitable means to the distal end of the control rod 250 adjacent to the weld 202a.

Figure 24:
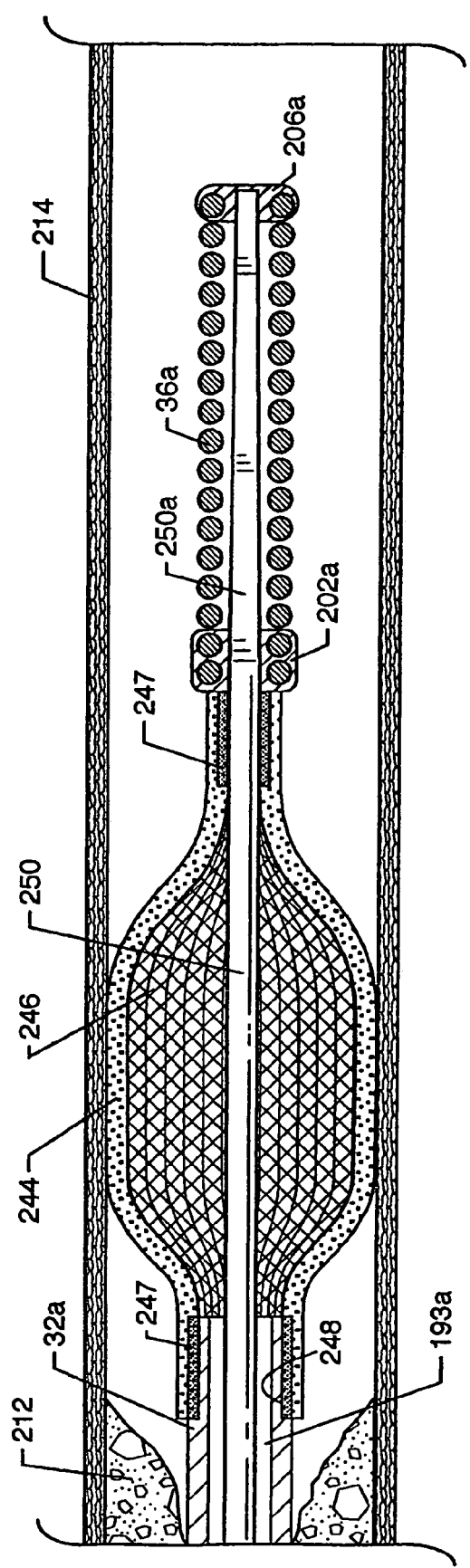
FIG. 24 is a view illustrating the use of the elements of FIG. 23.

FIG. 24 is a view in cross section illustrating the use of the elements of FIG. 23 where the controllable-shape mesh occluder 244 and the occluder guidewire tube 32a and associated components are loaded through the guide catheter 30 (not shown) and utilized in lieu of the balloon occluder 34 and the occluder guidewire tube 32. As no inflation of a balloon is required, the balloon inflation source 12 of FIG. 1 is not utilized. Several loading and positioning techniques can be utilized. In a first technique, if the controllable-shape mesh occluder 244 includes mesh 246 which does not exhibit positional memory, the control rod 250 is simply advanced a suitable distance distally, thereby pulling the attached controllable-shape mesh occluder 244, which maintains a low profile because of tension along the controllable-shape mesh occluder 244, and the attached occluder guidewire tube 32a through the guide catheter 30.

In a second technique, whether the mesh 246 exhibits or does not exhibit positional memory, loading is accomplished in the following manner. Prior to and/or during loading, the physician operator controls the relationship of and positions the control rod 250 in a distal direction with respect to the occluder guidewire tube 32a to cause the controllable-shape mesh occluder 244 to assume and maintain a collapsed low profile, as shown in FIG. 23, followed by unitary advancement of the guidewire coil 36a, the low profile controllable-shape mesh occluder 244, and the distal end of the occluder guidewire tube 32a distally beyond the thrombus 212 to a position such as shown in FIG. 14. Then after either loading technique is utilized, the occluder guidewire tube 32a is held steady and the control rod is retracted proximally a sufficient distance to cause expansion and distention of the controllable-shape mesh occluder 244 to be compliant with and to occlude the blood vessel 214 or other blood carrying structure where the occluding relationship of the occluder guidewire tube 32a and the controllable-shape mesh occluder 244 is maintained and is then unitarily retracted proximally to urge thrombus 212 in a proximal direction juxtaposing the subsequently loaded retractable capture cone 56 and capture catheter 40 and other components for maceration according to the teachings of the invention. Upon completion of the procedure the control rod 250 can be repositioned distally with respect to the occluder guidewire tube 32a to collapse the controllable-shape mesh occluder 244 and to withdraw the guidewire coil 36a, the low profile controllable-shape mesh occluder 244, and the distal end of the occluder guidewire tube 32a unitarily.

Figure 25:
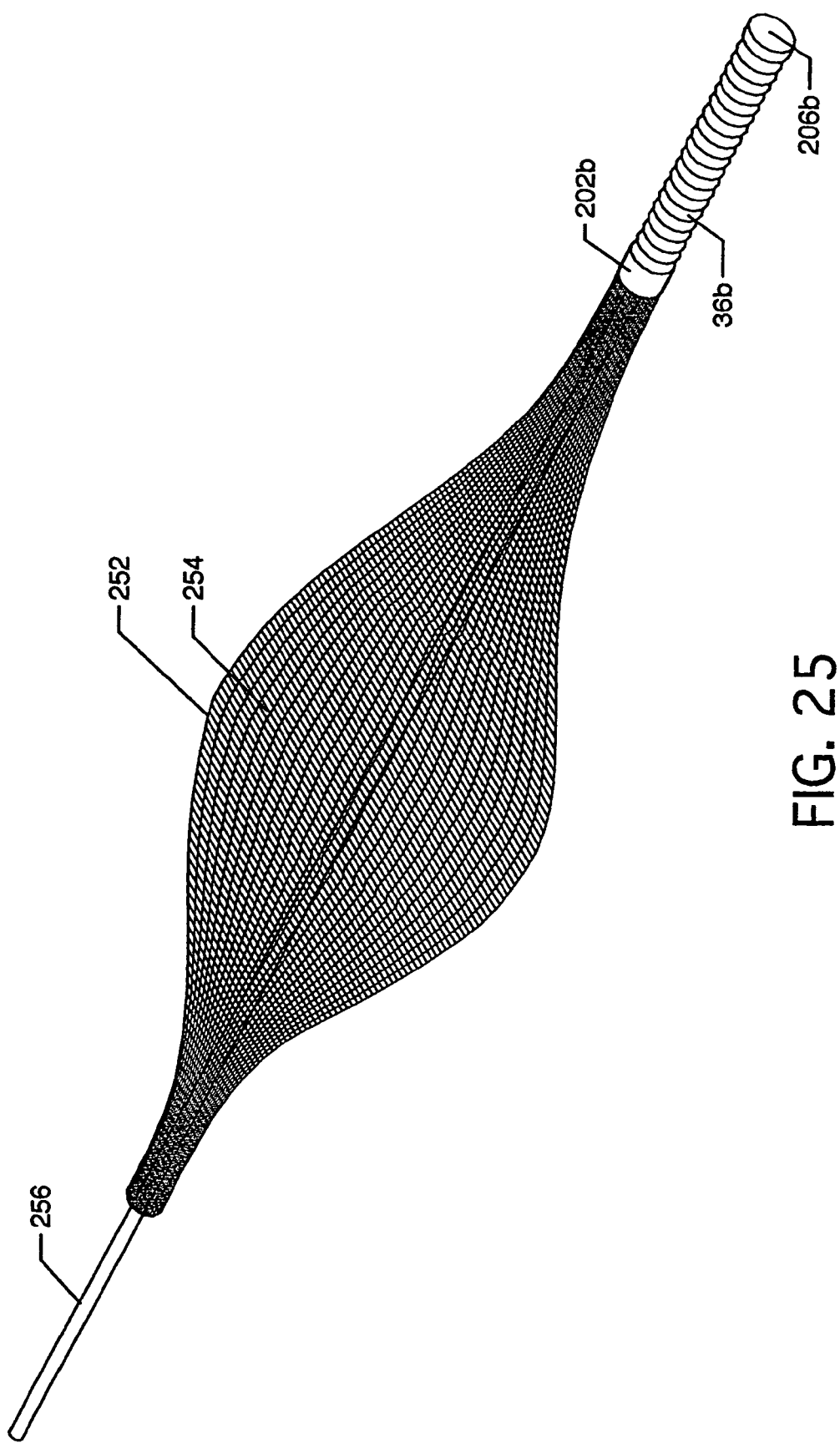
FIG. 25 is an isometric view of an alternative embodiment incorporating a flexible shaped mesh occluder.

FIG. 25 is an isometric view of an alternative embodiment incorporating an occluder having structure substantially similar to and performing the same thrombotic influencing function as the previously described inflated balloon occluder 34. Shown in particular is a flexible shaped mesh occluder 252 which is not inflatable but has a predetermined shape which is flexible, compressible, and utilizes positional memory to maintain a balloon-like shape suitable for occluding a blood vessel and for urging thrombotic material proximally for maceration. The flexible shaped mesh occluder 252 is fabricated of mesh 254, which can be a braid, a weave, or other interlacing strands or the like of metallic or non-metallic flexible materials which include position memory. The mesh 254 is of close-knit material, such as described above, which does not allow fluids to pass therethrough. The flexible shaped mesh occluder 252 can be utilized in lieu of the balloon occluder 34 previously described according to the teachings of the invention where the flexible shaped mesh occluder 252 is positioned and expandingly deployed to assume a shape generally resembling the balloon occluder 34.

Figure 26:
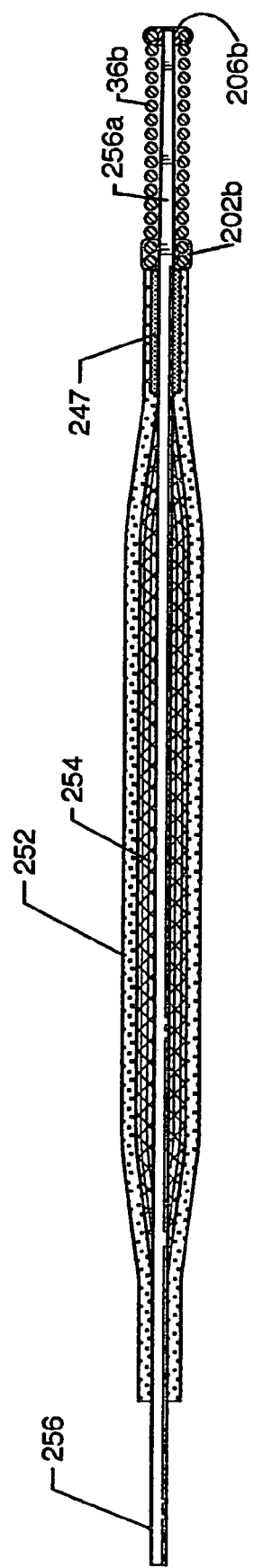
FIG. 26 is a cross section view of the embodiment of FIG. 25 showing the flexible shaped mesh occluder of FIG. 25 in a compressed state; and, FIG. 27 is a view illustrating the use of the elements of FIG. 26.

FIG. 26 is a cross section view of the embodiment of FIG. 25 showing the flexible shaped mesh occluder 252 in a compressed state forced to a low profile from positional memory such as for transferring through a lumen.

The flexible shaped mesh occluder 252 aligns over and about a control rod 256. The control rod 256 extends in the lumen 119 the length of the guide catheter 40 to exit the manifold 38 at the hemostasis nut 58 so that the physician operator may adjustably control the control rod 256. The distal portion of the control rod 256 which extends beyond the distal end of the flexible shaped mesh occluder 252 has the shape and characteristics of the tip of any coronary guidewire of the previously shown tapered flexible core 204 to form a tapered flexible core 256a. A weld 202b attaches the proximal end of a guidewire coil 36b to the proximal end of the tapered flexible core 256a, and a weld 206b attaches the distal end of the guidewire coil 36b to the distal end of the tapered flexible core 256a. In the alternative, the control rod 256 and the tapered flexible core 256a could be separate elements mutually joined with the guidewire coil 36b at weld 202b. The distal end of the flexible shaped mesh occluder 252 suitably attaches, such as by use of adhesive 247 or other suitable means, to the distal end of the control rod 256 adjacent the weld 202b. The proximal end of the flexible shaped mesh occluder 252 slidingly aligns to the control rod 256 and is free to position thereupon, thereby allowing the geometry of the flexible shaped mesh occluder 252 to be varied.

Figure 27:
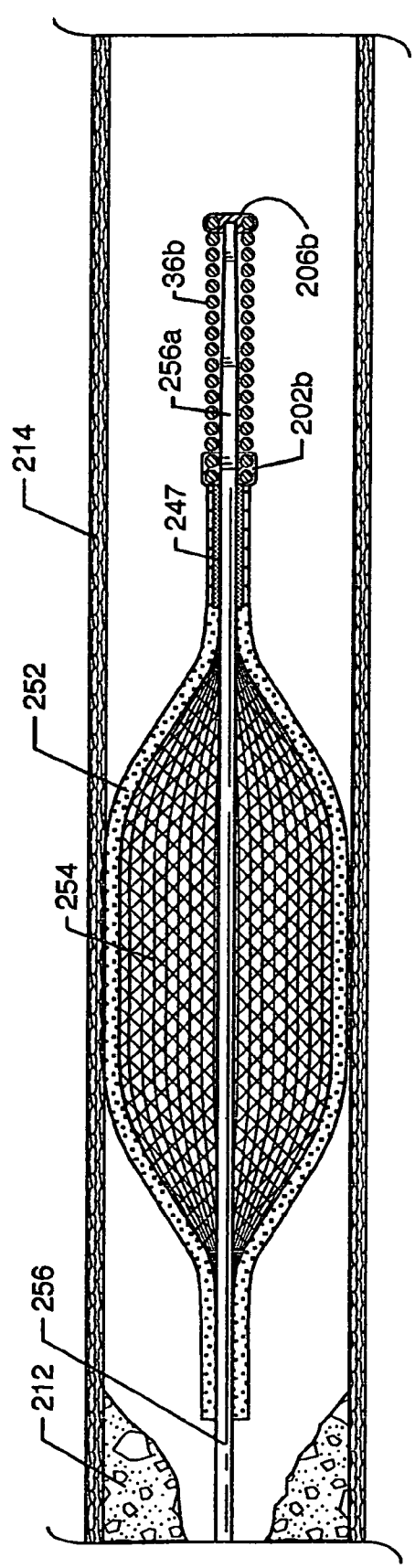

FIG. 27 is a view illustrating the use of the elements of FIG. 26 where the flexible shaped mesh occluder 252, the control rod 256, and associated components are utilized in lieu of the balloon occluder 34 and the occluder guidewire tube 32. As no inflation of a balloon is required, the balloon inflation source 12 of FIG. 1 is not utilized. The flexible shaped mesh occluder 252, the control rod 256, and associated components are introduced into the blood vessel 214 through the guide catheter 30 (not shown) where the distal end of the guide catheter 30 is first positioned through and distal to the thrombus 212.

Initially during use of the flexible shaped mesh occluder 252, the flexible shaped mesh occluder 252 is compressed to assume a low profile, as shown in FIG. 26, for insertion into the manifold 38, the capture catheter 40, the manifold 18 and the guide catheter 30. During loading the physician operator controls the relationship of and positions the control rod 256 in a distal direction with respect to the guide catheter 30 where the flexible shaped mesh occluder 252 continues to assume and maintain a collapsed low profile as shown in FIG. 26 followed by unitary advancement of the guidewire coil 36b, the low profile compressed flexible shaped mesh occluder 252, and the distal end of the control rod 256 distally to a position just short of the distal end of the guide catheter 30 but beyond the thrombus 212. Thus, a short distal portion of the guide catheter 30 distal to the thrombus 212 contains the guidewire coil 36*b*, the low profile flexible shaped mesh occluder 252 and the distal end of the control rod 256. Then after such loading, the control rod 256 is held steady and the guide catheter 30 is positioned proximally a sufficient distance to disengage from surrounding and encompassing contact with the flexible shaped mesh occluder 252 allowing expansion and distention of the flexible shaped mesh occluder 252 to be compliant with and to occlude the blood vessel 214 or other blood carrying structure where the occluding relationship of the control rod 256 and the flexible shaped mesh occluder 252 is maintained with the blood vessel 214 and is then unitarily retracted proximally to urge thrombus 212 in a proximal direction juxtaposing the subsequently loaded retractable capture cone 56 and capture catheter 40 and other components for maceration according to the teachings of the invention. Upon completion of the procedure, the guide catheter 30 can be advanced distally and the control rod 256 can be repositioned proximally with respect to guide catheter 30 to engage and collapse and compress the flexible shaped mesh occluder 252 and withdraw the guidewire coil 36*b*, the low profile compressed flexible shaped mesh occluder 252, and the distal end of the control rod 256 unitarily.

Various modifications can be made to the present invention without departing from the apparent scope thereof.

What is claimed is:

1. A method for thrombectomy comprising the steps of:
   a. providing a guide catheter, the guide catheter having a distal end and a proximally situated manifold with a hemostasis nut and a lumen, and providing an occluder guidewire tube having a proximal end and a distal end, with a guidewire coil and an occluder at the distal end, and providing a capture catheter, the capture catheter having a distal end with a retractable capture cone and a fluid jet emanator affixed thereto, the fluid jet emanator including at least one proximally directed jet orifice, and a proximally located manifold, the proximally located manifold having an exhaust branch, a high pressure connection branch, and a hemostasis valve adapted for passage of the occluder guidewire tube;
   b. advancing the distal end of the guide catheter into a vessel to a position adjacent to and proximal to a thrombus buildup;
   c. loading and advancing the distal end of the occluder guidewire tube through the hemostasis nut and into and through the manifold of the guide catheter and thence through the lumen of the guide catheter;
   d. advancing the distal end of the occluder guidewire tube, including the guidewire coil and the occluder, beyond the distal end of the guide catheter and through and beyond the thrombus buildup;
   e. loading the distal end of the capture catheter, including the retractable capture cone and the fluid jet emanator over the proximal end of the occluder guidewire tube;
   f. expanding the occluder to occlude the vessel;
   g. positioning the capture catheter to an appropriate position and expandingly deploying the retractable capture cone adjacent to and just beyond the distal end of the guide catheter, thereby isolating the thrombus in the vessel between the deployed retractable capture cone and the expanded occluder;
   h. providing and activating a high pressure medium to the fluid jet emanator so as to form rearwardly directed fluid jets;
   i. macerating, dislodging, reducing, and breaking up the thrombus with the fluid jets; and,
   j. evacuating the macerated, dislodged, reduced and broken-up thrombus.

2. The thrombectomy method of claim 1, further comprising the step of repositioning the expanded occluder proximally to impinge, impact, dislodge, reshape and redistribute thrombus and to urge and deliver such thrombus into the retractable capture cone.

3. The thrombectomy method of claim 2, wherein the step of repositioning includes manipulation of the manifold of the capture catheter.

4. The thrombectomy method of claim 2, wherein the step of repositioning is continued to near impingement of the occluder with the retractable capture cone.

5. The thrombectomy method of claim 1, wherein the vessel is a blood vessel.

6. The thrombectomy method of claim 5, wherein the blood vessel is a vein or an artery.

7. The thrombectomy method of claim 1, further comprising the step of monitoring the position of the guide catheter distal end with fluoroscopy.

8. The thrombectomy method of claim 1, further comprising the step of manipulating the manifold of the guide catheter while advancing the guide catheter.

9. The thrombectomy method of claim 1, wherein the at least one jet orifice is one of a plurality of jet orifices.

10. The thrombectomy method of claim 1, further comprising the step of collapsing the occluder subsequent to removing the thrombus.

11. The thrombectomy method of claim 10, further comprising the step of withdrawing the collapsed occluder through the retractable capture cone.

12. The thrombectomy method of claim 11, further comprising the step of retracting the retractable capture cone proximally to retractably collapse the retractable capture cone to conform to the guide catheter.

13. The thrombectomy method of claim 12, further comprising the step of withdrawing the guide catheter, the capture catheter, and the occluder guidewire tube simultaneously.

14. The thrombectomy method of claim 12, further comprising the step repositioning the guide catheter, the capture catheter, and the occluder guidewire tube simultaneously and distally to adjacent to and proximal to another thrombus site, to prepare for additional thrombus removal.

15. A system for thrombectomy comprising:
   a. a guide catheter, the guide catheter having a distal end and a proximally situated manifold with a hemostasis nut and a lumen;
   b. an occluder guidewire tube having a proximal end and a distal end, with a guidewire coil and an occluder at the distal end; and,
   c. a capture catheter, the capture catheter having a distal end with a retractable capture cone and a fluid jet emanator affixed thereto, the fluid jet emanator including at least one proximally directed jet orifice, and the capture catheter having a proximally located manifold, the proximally located manifold having an exhaust branch, a high pressure connection branch, and a hemostasis valve adapted for passage of the occluder guidewire tube; wherewith fluid and thrombus may be isolated in the vasculature between the retractable capture cone, when deployed, and the occluder, when expanded, then disrupted and macerated by action of fluid jets, for removal from the body by suction applied at the retractable capture cone, thereby avoiding undesired release of thrombus portions within the vasculature.

16. The system as defined in claim 15, wherein the occluder is an inflatable balloon.

17. The system as defined in claim 15, wherein the occluder is a controllable-shape mesh.

18. The system as defined in claim 15, wherein the occluder is a flexible shaped mesh.

19. The system as defined in claim 15, wherein the retractable capture cone comprises a position memory material.

20. The system as defined in claim 15, further comprising a plurality of expansion struts.

21. The system as defined in claim 20, wherein the plurality of expansion struts comprise a position memory material.

22. The system as defined in claim 15, wherein the fluid jet emanator is configured to entrain thrombus and thrombus debris.

23. The system as defined in claim 15, wherein the fluid jet emanator is configured so that the at least one proximally directed jet aids in carrying thrombus debris proximally for collection.

24. A system for thrombectomy comprising:
   a. a guide catheter, the guide catheter having a distal end and a lumen;
   b. an occluder guidewire tube having a proximal end and a distal end, with a guidewire coil and an occluder at the distal end;
   c. a capture catheter, the capture catheter having a distal end with a retractable capture cone and a fluid jet emanator, the fluid jet emanator affixed to the capture catheter and including a plurality of proximally directed jet orifices, and the capture catheter further having a proximally located manifold, the manifold having an exhaust branch, a high pressure connection branch, and a hemostasis valve, and a lumen communicating between the distal end of the capture catheter and exhaust branch and a high pressure lumen communicating between the high pressure connection branch and the fluid jet emanator affixed to the capture catheter;
   d. the capture catheter configured to pass through the lumen of the guide catheter, wherein the retractable capture cone is held in a retracted position when inside the lumen of the guide catheter;
   e. the occluder guidewire tube configured to pass through the lumen of the capture catheter, so that the plurality of proximally directed jet orifices are disposed about the guidewire tube; and,
   f. wherewith fluid and thrombus may be isolated in the vasculature between the retractable capture cone, when deployed, and the occluder, when expanded, then disrupted and macerated by action of fluid jets, for removal from the body by suction applied at the retractable capture cone, thereby avoiding undesired release of thrombus portions within the vasculature.

* * * * *